US 12,053,640 B2

(12) United States Patent
Thorhauge et al.

(10) Patent No.: US 12,053,640 B2
(45) Date of Patent: Aug. 6, 2024

(54) MEDICAL LASER SYSTEM

(71) Applicant: Advalight ApS, Ballerup (DK)

(72) Inventors: Morten Thorhauge, Bagsværd (DK);
Jesper Liltorp Mortensen, Glostrup (DK); Kasper Vikkelsø Seidler, Bjæverskov (DK)

(73) Assignee: Advalight ApS, Ballerup (DK)

( * ) Notice: Subject to any disclaimer, the term of this patent is extended or adjusted under 35 U.S.C. 154(b) by 798 days.

(21) Appl. No.: 17/253,039

(22) PCT Filed: Apr. 30, 2019

(86) PCT No.: PCT/EP2019/061045
§ 371 (c)(1),
(2) Date: Dec. 16, 2020

(87) PCT Pub. No.: WO2019/242919
PCT Pub. Date: Dec. 26, 2019

(65) Prior Publication Data
US 2021/0260401 A1    Aug. 26, 2021

(30) Foreign Application Priority Data

Jun. 18, 2018   (EP) .................................... 18178169

(51) Int. Cl.
*A61N 5/067*   (2006.01)
*A61N 5/06*    (2006.01)
*A61N 5/073*   (2006.01)

(52) U.S. Cl.
CPC .... *A61N 5/0616* (2013.01); *A61N 2005/0628* (2013.01); *A61N 2005/0659* (2013.01);
(Continued)

(58) Field of Classification Search
None
See application file for complete search history.

(56) References Cited

U.S. PATENT DOCUMENTS 7,961,772 B2 * 6/2011 Tidemand-Lichtenberg ...............
H01S 3/1312
372/29.011
2007/0160093 A1    7/2007 Nishizawa
(Continued)

FOREIGN PATENT DOCUMENTS

JP    H05-110179 A    4/1993

OTHER PUBLICATIONS

International Search Report and Written Opinion of International Searching Authority for Application No. PCT/EP2019/061045, mailed Aug. 5, 2019 (8 pages).

*Primary Examiner* — Kennedy Schaetzle
(74) *Attorney, Agent, or Firm* — Nixon Peabody LLP

(57) ABSTRACT

A medical laser system including a first laser source having a first gain medium for generating a first optical field. The system further includes a first Q-switch controlling a resonance quality of the first laser source, a control circuit controlling the first Q-switch to cause the first laser source to generate the first optical field as a first pulse train of laser pulses, a second laser source for generating a second optical field as a second pulse train of laser pulses, a nonlinear medium for generating a third optical field by a nonlinear interaction between the first optical field and the second optical field, and a sensor detecting a property of at least one of the optical fields. The control circuit controls operation of the first Q-switch so as to adjust a relative timing of the laser pulses of the first pulse train and the laser pulses of the second pulse train responsive to the detected property.

25 Claims, 7 Drawing Sheets

(52) U.S. Cl.
CPC ...... *A61N 2005/0663* (2013.01); *A61N 5/067* (2021.08); *A61N 2005/073* (2013.01)

(56) References Cited

U.S. PATENT DOCUMENTS

| | | |
|---|---|---|
| 2010/0002732 A1 | 1/2010 | Tidemand-Lichtenberg |
| 2011/0306955 A1 | 12/2011 | Thorhauge |
| 2012/0044959 A1 | 2/2012 | Zhao |

* cited by examiner

MEDICAL LASER SYSTEM

CROSS-REFERENCE TO RELATED APPLICATIONS

This application is a U.S. National Stage of International Application No. PCT/EP2019/061045, filed Apr. 30, 2019, which claims the benefit of European Patent Application No. 18178169.1, filed Jun. 18, 2018, both of which are incorporated herein by reference in their entireties.

TECHNICAL FIELD

The present disclosure relates to a medical laser system, in particular a medical laser system for the cosmetic treatment of skin conditions, and to a method for controlling a medical laser system.

BACKGROUND

Medical laser systems are widely used for numerous medical applications, such as for surgery or therapy of various diseases. Medical laser systems are also used for cosmetic treatment of skin conditions.

Due to the increased focus on appearance today one of the central areas for cosmetic treatments of skin conditions is related to so-called rejuvenation. Skin can be affected by a range of biological and ageing effects, and by environmentally induced damages, such as wrinkles, acne, sun damage, reddening, vascular disorders and scarring. Rejuvenation is the combined area of treating these conditions in order to restore the youthful appearance of the skin. One of the most preferred treatments for skin rejuvenation is light-based treatment, also referred to as photo rejuvenation.

US 2011/0306955 discloses a laser system for skin treatment. This prior art laser system comprises a first and a second laser resonator. The first laser resonator comprises at least a first gain medium for generating a first optical field along a first optical axis; the second laser resonator comprises at least a second gain medium for generating a second optical field along a second optical axis. The laser system further comprises at least one nonlinear medium for generating a third optical field along a third optical axis by a nonlinear interaction between the first optical field and the second optical field, and at least one optical pump source for optically pumping the first gain medium and the second gain. Moreover, this prior art laser system comprises a first Q-switch in the first laser resonator and a second Q-switch in the second laser resonator. The Q-switches are capable of controlling a resonance quality of the first laser resonator and/or second laser resonator, respectively. In this way, light emission from the first and/or second laser resonator may be controlled to provide optical pulses at the first, second, and/or third wavelength.

In such laser system the conversion of the first and second optical fields into the third optical field requires the pulses of the first and second optical fields to be synchronized in the nonlinear medium. While such synchronization may be based on geometrical design and optical parameters of individual laser cavities this is difficult to stabilize and manufacture. Moreover, pulsing pump sources are generally not an option for solid state lasers due to long stabilization time.

U.S. Pat. No. 7,961,772 discloses a laser system in which the pulse overlap between two or more laser lines of the system is optimizable. To this end at least a part of the output is fed back to a regulation system which regulates the build-up time of individual laser pulses of the first and second optical fields by controlling the intensity output of the pump sources.

As the properties of the gain media, nonlinear media and/or pump sources may vary over time, an efficient conversion requires careful control of the laser system. While the above prior art laser system provides a method for controlling the temporal pulse overlap, there remains a need for a laser system and for a control method that provide a higher degree of robustness against drift, e.g. due to temperature variations and part degradation. In particular, the above prior art system imposes high requirements on the hardware employed. This increases manufacturing costs as there may often be statistical tolerances in components. For example, the gain material figure of merit may affect pulse synchronization/timing. Moreover, properties of the components may vary over time due to dynamic factors such as part degradation, accidental misalignment, temperature variations, etc.

As the prior art system controls the temporal overlap by controlling the pump sources, the output power of the system may be affected by the control of the temporal pulse overlap. Therefore, controlling the pulse overlap may become increasingly difficult without undesired loss of output power when the two laser resonators drift relatively far apart.

It thus remains desirable to provide a medical laser system and a control method for such a medical laser system that addresses one or more of the above needs and/or other needs that exist in the field of medical laser systems.

SUMMARY

According to one aspect, disclosed herein are embodiments of a medical laser system, comprising:
  a first laser source comprising a first laser resonator, at least one first gain medium for generating a first optical field; and at least one first Q-switch configured to control a resonance quality of the first laser resonator;
  a control circuit configured to control the first Q-switch to cause the first laser resonator to generate the first optical field as a first pulse train of laser pulses;
  a second laser source for generating a second optical field as a second pulse train of laser pulses;
  at least one nonlinear medium for generating at least a third optical field by a nonlinear interaction between the first optical field and the second optical field;
  at least one sensor circuit configured to detect a property of at least one of the optical fields;
  wherein the control circuit is configured to control operation of the first Q-switch so as to adjust a relative timing of the laser pulses of the first pulse train and the laser pulses of the second pulse train responsive to the detected property.

The inventors have realized that the temporal overlap between pulses of the respective first and second optical fields can accurately be adjusted by controlling operation of the first Q-switch based on detected properties of at least one of the optical fields. In particular, it has turned out, that an accurate, real-time adjustment may be performed even in situations where laser components drift considerably over time. Moreover, the adjustment does not negatively influence the output power.

In some embodiments, the control circuit comprises an adjustable delay circuit; wherein the control circuit is configured to generate a trigger signal and to forward the trigger signal to the adjustable delay circuit; wherein the adjustable delay circuit is configured to forward a delayed version of the trigger signal, delayed by an adjustable delay relative to the trigger signal, to the first Q-switch; and wherein the control circuit is configured to adjust the adjustable delay responsive to the detected property. Accordingly, an efficient and stable control mechanism is provided that allows real-time synchronization of the laser pulses even in situations where the individual laser components experience strong drift. The trigger signal may be, or at least be derived from, a clock signal or another suitable periodic signal. Accordingly, the control circuit may comprise a master clock operable to generate a clock signal. The clock signal may be forwarded to the delay circuit which forwards a delayed trigger signal to the first Q-switch.

In some embodiments, the detected property represents an output power of the third optical field. Accordingly, the relative timing of the pulses of the first and second optical fields may be controlled so as to increase, in particular so as to maximize, the detected output power. This control mechanism provides a relatively low-complex control method. The output power may e.g. be measured by a photodetector, i.e. the sensor circuit may comprise a photodetector. To this end, a minor portion of the third optical field may be directed towards the photodetector, e.g. by means of a beam splitter. The sensor signal from the photodetector thus represents the output power of the third optical field and may be fed back to the control circuit. The control circuit may thus implement a suitable control mechanism for adjusting a relative delay between the pulses of the first and second pulse trains so as to maximize the output power of the generated third optical field.

In some embodiments, the detected property represents a relative timing of the laser pulses of the first pulse train and the laser pulses of the second pulse train. For example, the sensor circuit may comprise one or more photodetectors for detecting the pulses of the first and second pulse trains and circuitry for detecting a time lag between the detected pulses of the first and second pulse trains. A sensor signal representing the detected time lag may then be fed back to the control circuit and the control circuit may adjust the delay of the trigger signal to the first Q-switch so as to minimize the detected time lag. Consequently, the control circuit may continuously detect the time lag and determine a corresponding delay suitable for compensating for the detected time lag, even when currently no third optical field is created in the nonlinear medium. This allows the control circuit to establish the correct trigger delay when generation of the third optical field is again desired, i.e. a fast turning on of the third optical field at optimized output power may be achieved even in situations when the required trigger delay changes over time.

The pulses of the first pulse train have a first pulse width and a first pulse repetition rate. Generally, the pulse width may be defined as a full width at half maximum of the pulses. The first pulse width and the first pulse repetition rate together define a first gap width between consecutive pulses of the first pulse train. In some embodiments, the first pulse width is smaller than the first gap width, such as less than 50% of the first gap width, such as less than 10% of the first gap width, such as less than 1% of the first gap width, e.g. between 0.01% and 1% of the first gap width. Similarly, the pulses of the second pulse train have a second pulse width and a second pulse repetition rate. The second pulse width and the second pulse repetition rate together define a second gap width between consecutive pulses of the second pulse train. In some embodiments, the second pulse width is smaller than the second gap width, such as less than 50% of the second gap width, such as less than 10% of the second gap width, such as less than 1% of the second gap width, e.g. between 0.01% and 1% of the second gap width.

In some embodiments, the pulse widths and repetition rates of the first and second pulse trains may be selected such that the pulses of the first pulse train, when aligned with respective gaps between pulses of the second pulse train, do not overlap in time with pulses from the second pulse train. Similarly, the pulse widths and repetition rates of the first and second pulse trains may be selected such that the pulses of the second pulse train, when aligned with respective gaps between pulses of the first pulse train, do not overlap in time with pulses from the first pulse train. In particular, in some embodiments, the second pulse width is smaller than the first gap width, such as less than 50% of the first gap width, such as less than 10% of the first gap width, such as less than 1% of the first gap width, e.g. between 0.01% and 1% of the first gap width. Likewise, in some embodiments, the first pulse width is smaller than the second gap width, such as less than 50% of the second gap width, such as less than 10% of the second gap width, such as less than 1% of the second gap width, e.g. between 0.01% and 1% of the second gap width.

The pulse width of the pulses of the first train and/or the second pulse train may be between 30 ns and 100 ns, such as between 4 ns and 60 ns. The gap width of the pulses of the first train and/or the second pulse train may be between 0.01 µs and 500 µs, such as between 0.1 µs and 300 µs, such as between 1 µs and 200 µs, such as between 10 µs and 100 µs, such as between 50 µs and 100 µs.

In some embodiments, the first pulse width and the second pulse width are substantially the same. Similarly, the first pulse repetition rate and the second pulse repetition rate may be substantially the same or at least chosen such that their ratio is a rational number such as an integer.

Generally, the control circuit may be configured to control the relative timing such that the laser pulses of the first pulse train temporally overlap in the nonlinear medium with respective laser pulses of the second pulse train, at least when generation of the third optical field is desired, e.g. responsive to a command to turn on the third optical field and/or so as to generate bursts of the third optical field. The degree of temporal overlap should be sufficient to allow the nonlinear process for generating the third optical field to occur in the nonlinear medium, i.e. pulses of the first pulse train should coincide with respective pulses of the second pulse train inside the nonlinear medium. While, in some embodiments, it may be most preferable when the relative timing is such that the pulses of the first pulse train perfectly coincide, i.e. are perfectly synchronized with, respective pulses of the second pulse train inside the nonlinear medium, lesser degrees of temporal overlap may in some embodiments be acceptable.

Generally, in medical laser systems, e.g. in laser systems for skin treatment, there often is a need for providing the output laser beam as short bursts. To this end the above laser systems typically include a mechanical shutter. However, such shutters have relatively slow reaction time and they impose limits on how short bursts/pulse trains may be emitted due to restrictions on mechanical movement and speed. Alternative methods include electro-optical and acousto-optical devices with or without additional optics e.g. polarization optics. These active optical methods introduce additional lossy and costly components in the beam path and suffer from other disadvantages. For example, electro-optical devices involve high tension drivers while acousto-optical devices may involve poor suppression for limited excitation power. Additionally, these devices may unintentionally affect other wavelengths delivered by the laser system.

Accordingly, in some embodiments, the control circuit is configured to control the relative timing so as to selectively cause generation of the third optical field, i.e. the control circuit may be configured to be operable as an exposure control device, such as a shutter, so as to only selectively cause generation of the third optical field, e.g. responsive to respective exposure/shutter commands. In particular, in some embodiments, the control circuit is configured, responsive to a first signal, to selectively control the relative timing such that the laser pulses of the first pulse train temporally overlap in the nonlinear medium with respective laser pulses of the second pulse train so as to cause generation of the third optical field; and wherein the control circuit is configured, responsive to a second signal, to selectively control the relative timing such that the laser pulses of the first pulse train do not temporally overlap in the nonlinear medium with respective laser pulses of the second pulse train so as to prevent generation of the third optical field. For example, the first signal may be indicative of an "open shutter" command while the second signal may be indicative of a "close shutter" command. Alternatively, or additionally, the first and second signals may be provided as periodic signals, e.g. a clock signal, for controlling the intermittent/periodic creation of short bursts of pulsed laser light.

It has turned out that this control method allows very fast reaction times and the creation of small burst of pulsed laser output, e.g. of bursts smaller than 10 ms, such as 1 ms or less. Accordingly, some embodiments of the medical laser system provide a temporal control of the generated third optical field, where the temporal control is performed on a time scale of less than 10 ms, such as 1 ms or less.

In some embodiments, in particular when the detected property represents a relative timing of the laser pulses of the first pulse train and the laser pulses of the second pulse train, the control circuit may receive information about an adequate timing of pulses even during a period where no third optical field is generated. This may be the case during a period where the control circuit is configured to control the relative timing to be a first relative timing that causes the laser pulses of the first pulse train to not temporally overlap in the nonlinear medium with respective laser pulses of the second pulse train so as to prevent generation of the third optical field. The control circuit may still determine a second relative timing that would, if applied, cause the laser pulses of the first pulse train to temporally overlap in the nonlinear medium with respective laser pulses of the second pulse train so as to cause generation of the third optical field. Accordingly, responsive to a signal (e.g. an open shutter command), the control circuit may switch the applied relative timing from the first relative timing to the determined second relative timing so as to cause a fast turning on of the third optical field at optimized output power. To this end, the control circuit may determine a suitable delay of the trigger signal to the first Q-switch that causes the pulses of the first and second pulse trains to temporally overlap in the nonlinear medium even during periods when the applied relative delay is selected such that currently the pulses do not temporally overlap and no third optical field is generated.

In some embodiments, the control circuit is operable as a wavelength selector. To this end, the first optical field may have a first wavelength, the second optical field may have a second wavelength and the third optical field may have a third wavelength different from the first and second wavelengths. The control circuit may then be configured, e.g. responsive to a wavelength selection command, to selectively control the relative timing so as to control a wavelength of an output radiation of the laser system, e.g. so as to selectively include the third optical field in an output from the laser system. In particular, when the pulses of the first and second pulse trains temporally overlap in the nonlinear medium, the third optical field is generated in the nonlinear medium, and the output from the nonlinear medium includes a major amount of light of the third wavelength and lesser amounts of light of the first and second wavelengths. Conversely, when the pulses of the first and second pulse trains do not temporally overlap, the first and second optical fields propagate through the nonlinear medium without generating the third optical field. Hence, the output from the nonlinear medium is then composed of the pulse trains of the first and second optical fields, i.e. at the first and second wavelengths. Accordingly, by selectively causing the nonlinear process for generating the third optical field to occur, the system may switch between a laser output that includes the third wavelength and a laser output that only includes the first and second wavelengths. It will be appreciated that, in some embodiments, it may be possible to completely suppress generation of the third optical field, namely by appropriate temporal misalignment of the pulses in the nonlinear medium. However, when the temporal overlap is adjusted such that the third optical field is generated, the output of the nonlinear medium will typically still include contributions of the first and/or second optical field, though typically to a lesser extent. The first and second wavelengths may be the same or they may be different from each other. In the latter case, the medical laser system may further include one or more output selectors for selecting the first optical field, and/or the second optical field, and/or the third optical field to be delivered to the output port. In this way, the relevant wavelengths for skin treatment may be delivered to an output port of the medical laser system, while any unwanted wavelengths may be blocked.

Embodiments of the medical laser system disclosed herein allow a very fast switching between output radiation that includes the third optical field and output radiation that only includes the first and second optical field. If selection between the first and second optical fields is desired, or a substantially complete suppression of the first and second optical fields is desired, this may be achieved by output selectors, e.g. additional filters, mirrors, or other devices e.g. shutters in the beam paths of the first and/or second optical fields. In some embodiments, the wavelength selection by controlling the temporal pulse overlap in the nonlinear medium reduces or even eliminates the need for additional output selectors.

Nevertheless, the laser system may include one or more output selectors. The output selector may include one or more optical filters, e.g. a high-pass, low-pass or band-pass filer, configured to selectively block the first and/or second wavelength and/or third wavelength. In particular, in some embodiments, the medical laser system comprises one or more output selectors for selectively blocking radiation of the first and/or second wavelength and/or third wavelength to be included in the output radiation of the laser system; the control circuit may thus be configured to selectively activate the output selector(s) in response to a wavelength selection command, e.g. by selectively moving the output selector(s) into or out of the beam path of the output from the nonlinear medium and/or otherwise moving, e.g. rotating, the output selector between an active and an inactive state. The output selector may be used for wavelength selection instead of the wavelength selection based on the selective synchronization of the laser pulses, or it may be used as an additional output selector. The output selector may be controllable to be selectively brought into a first state and a second state. When the output selector is in the first state, a first selection of one or more of the first, second and third wavelengths is allowed to pass the output selector. When the output selector is in the second state, a second selection of one or more of the first, second and third wavelengths is allowed to pass the output selector, the second selection being different from the first selection. It will be appreciated that some embodiments of an output selector may have two or more states so as to allow selection of multiple subsets of wavelengths to either be blocked or allowed to pass.

In some embodiments, the output selector comprises a mirror selector and a plurality of selection mirrors, the mirror selector being configured to selectively position any of the selection mirrors so that the incident first optical field, second optical field and third optical field are divided into reflected fields and transmitted fields, and wherein at least one of the reflected fields or the transmitted fields is/are delivered to the output port. Thus, by using a plurality of selection mirrors having different reflectance and/or transmittance at the first, second and third wavelength, the wavelengths delivered to the output port may be controlled. In this way, an output selector is achieved, which is particularly suitable for high optical peak powers. In alternative embodiments, the output selector may comprise one or more gratings or other devices for spatially separating the first, second, and third optical fields, individually or in combinations.

The skilled person will appreciate that the mirror selector may be driven in a multitude of ways, e.g. manually by a dial, by a stepper motor, by a gear.

While the selective control of the temporal pulse overlap in the nonlinear medium allows for a fast and efficient exposure control and reduces, or even eliminates, the need for an additional exposure control device, it will be appreciated that some embodiments of the medical laser system disclosed herein may nevertheless comprise an exposure control device. The exposure control device may be used for exposure control instead of the exposure control based on the selective synchronization of the laser pulses, or it may be used as an additional exposure control. Examples of suitable exposure control devices are a mechanical shutter, an acousto-optical device capable of deflecting the emitted beam onto a beam dump, an electro-optical device capable of altering the polarization state of the beam in combination with a device capable of passing a given polarization state onto the output port of the laser system, while being capable of deflecting the orthogonal polarization state onto a beam dump.

In some embodiments, the laser system comprises an exposure control device and an output selector, e.g. controllable by the control circuit. In some embodiments, the control circuit may be configured, when activating the output selector in response to a wavelength selection command, to initially activate the exposure control device so as to block radiation from being emitted from the laser system before activating the output selector so as to selectively block and/or select one or more of the first, second and third wavelengths. The activation causes the state of the output selector to change from a first state to a second state, e.g. by moving a mirror, filter, etc. from one position and/or orientation to another position and/or orientation. Once the output selector has reached the second state, the control circuit may be configured to deactivate the exposure control device so as to allow radiation again to be emitted from the laser system.

The exposure control device may be a shutter, such as a mechanical shutter, and activating the exposure control device may involve closing the shutter while deactivating the exposure control device may involve opening the shutter.

In some embodiments the exposure control device may be positioned downstream from the output selector along the radiation path, in particular along the third optical axis. In other embodiments, the exposure control device may be positioned upstream from the output selector along the radiation path, in particular along the third optical axis. In the latter case, the exposure control device prevents, when activated, radiation to impinge on the output selector during the transition between respective states of the output selector. This may be beneficial in order to prevent components, e.g. filter or mirror mountings to be damaged when they are moved through the radiation path.

It will be appreciated that the first and second optical fields do not need to have different wavelengths. Alternatively, or additionally to different wavelengths, the first and second optical fields may differ from each other by one or more other parameters, e.g. by their polarization. Generally, two optical fields may differ from each other by one or more parameters. For example, they may have different wavelength and/or different polarization.

In some embodiments, the medical laser system comprises a hand-held radiation delivery device defining at least one optical output port for delivering said first and/or second and/or third optical field to an output. In some embodiments, the medical laser system is configured to selectively deliver said first, second and/or third optical fields by said optical output port. In particular, in some embodiments, the medical laser system is configured to selectively deliver said first, second and/or third optical fields to a plurality of target locations, e.g. so as to selectively deliver an optical field of different wavelengths to different target locations. It is an advantage of embodiments of the medical laser system described herein, that the generation of the third optical field may be selectively suppressed while the optical delivery system is adjusted so as to irradiate a new target location, e.g. by moving one or more optical components e.g. a mirror, so as to direct the output of the medical laser system to a new target location within the target area. Accordingly, irradiation of skin areas other than the desired target locations (e.g. while moving between target locations) is avoided.

In some embodiments, the hand-held radiation delivery device is optically connected to an output of the nonlinear medium by a beam delivery component. In this way, the optical output from the laser sources and the nonlinear medium may conveniently be delivered to a point of treatment on, e.g. the skin of a patient. In some embodiments, the beam delivery component comprises at least one of an optical waveguide, an optical fiber, an articulated arm, and/or at least a first delivery mirror. In this way, a particularly user-friendly laser system may be achieved. In an embodiment of the laser system, the fiber has a core diameter in the range from about 50 μm to about 1000 μm.

In some embodiments, the hand-held radiation delivery device may be configured for scanning the laser light in a pre-set pattern of individual target skin areas covering said treatment area. Alternatively, the treatment area may be a single target skin area.

In alternative embodiments, the radiation delivery device is not necessarily hand-held. Instead, the radiation delivery device may e.g. have the form of a fixture or mounting element for attaching, mounting or fixating the radiation delivery device relative to the target area, e.g. as a fixture to be attached or otherwise fixedly positioned relative to a patient's body.

For the purpose of the present description, the term Q-switch is intended to comprise any device operable to modulate a quality factor of the laser resonator. It will be appreciated that there are a variety of types of Q-switches, including e.g. active and passive Q-switches and/or Q-switches employing a variety of technologies.

In some embodiments, each of the first and second laser sources include a respective laser resonator and a respective Q-switch. The first Q-switch may be of the active type and the second Q-switch may be of the active or passive type.

In some embodiments, each of the first and second Q-switches is an active Q-switch. In some embodiments, each of the first and second Q-switches is controlled by the control circuit, e.g. triggered by a respective trigger signal provided by the control circuit. Thereby the first and second laser sources may be individually Q-switched so as to be operable as individually running pulsed laser emitters. Hence, in some embodiments, the control circuit is configured to control operation of the first and second Q-switches so as to adjust a relative timing of the laser pulses of the first pulse train and the laser pulses of the second pulse train responsive to the detected property. In particular, in some embodiments, the control circuit comprises an adjustable delay circuit; wherein the control circuit is configured to generate a trigger signal and to forward the trigger signal to one of the first and second Q-switches and to the adjustable delay circuit; wherein the adjustable delay circuit is configured to forward a delayed version of the trigger signal, delayed by an adjustable delay relative to the trigger signal, to the other one of the first and second Q-switches; and wherein the control circuit is configured to adjust the adjustable delay responsive to the detected property. The trigger signal may be generated by a master clock. The trigger signal may be forwarded to the first Q-switch and a delayed trigger signal to the second Q-switch or vice versa, i.e. the trigger signal may be forwarded to the second Q-switch and a delayed trigger signal to the first Q-switch.

In some embodiments, the second Q-switch is of the passive type. Suitable passive Q-switches may be any type of Q-switch comprising a medium with an initial transmittance and a final transmittance, wherein the change in transmittance is essentially caused by the optical intensity of the optical field propagating through the Q-switch. One example of such a passive Q-switch is a saturable absorber. In an embodiment of the medical laser system, the passive Q-switch comprises Cr:YAG, V:YAG, and/or Cr:Forsterite. This choice of passive Q-switch material is suitable for first and second wavelengths in the range 1000-1400 nm. Other choices of passive Q-switch materials are readily known by the skilled person, e.g. for use at other wavelengths. See for example: W. Koechner, "Solid-State Laser Engineering", Sixth Edition, Springer Inc., 2006.

A passive second Q-switch may thus be configured to provide a second pulse train of laser pulses of a predetermined pulse repetition rate, e.g. determined by the design of the second laser source. The second pulse train may thus be used as a clock signal based on which the control circuit is configured to generate the trigger signal for controlling the active first Q-switch.

Naturally, one may also envision a laser system, wherein one or both of the laser sources comprise one or more additional Q-switches, e.g. all additional Q-switches being passive, all being active, or some being passive and some being active.

Yet alternatively, the second laser source may be a different type of pulsed laser source for creating pulsed laser light, e.g. without employing a Q-switch. Generally, a pulsed laser source to which a Q-switched laser source may be synchronized for e.g. generating a third optical field, may be pulsed by other means than a Q-switch. Examples of such pulsed lasers are gain switched lasers, examples of which are gain switched semiconductor lasers. Gain switching may be achieved by e.g. modulating the drive current for a diode laser, or by modulating the optical pump/excitation light intensity for a semiconductor disc laser.

Another example of a gain switched laser may be a crystal-based laser or a glass-based laser gain material where the optical pump/excitation light may be intensity modulated.

In one embodiment, the second laser source to which a Q-switched laser source may be synchronized for generating a third optical field may include multiple stages of optical pulse generation and subsequent amplification e.g. a Master Oscillator Power Amplifier laser source. An example of such system is a fiber power amplifier seeded by a pulsed diode laser. In another example the power amplifier may be any other optical amplifier e.g. a crystal or glass gain media-based amplifier or a semiconductor-based amplifier.

In such embodiments, the control circuit may generate the clock signal for both the gain switched pulsed laser system and the Q-switched pulsed laser system. The delayed clock signal may likewise be routed to either the gain switched pulsed laser system, or to the Q-switched pulsed laser system, or delayed or processed clock signals may be routed to both the gain switched and the Q-switched laser systems.

In some embodiments, the second laser source comprises a second laser resonator and at least a second gain medium for generating the second optical field. The gain medium of the first and/or second laser resonator may be a crystal based, and/or glass based, and/or fiber based medium. For example, crystal-based gain materials may be in the shape of slabs, rods, blocks, fibers or thin disks. Generally, the gain medium of the first and second laser resonator may be configured to provide a gain at the first or second wavelength, respectively. Furthermore, the gain media may be configured to sustain the optical power level within a resonator of the corresponding laser source under operation.

In some embodiments, at least one of the first gain medium and/or the second gain medium comprise(s) a rare-earth doped crystal. Both the first gain medium and the second gain medium may comprise rare-earth doped crystals. Likewise, any additional gain media in a resonator of the first or second laser source may comprise rare-earth doped crystals. In alternative embodiments, the first gain medium and/or the second gain medium may be any of the following: a crystal, a gas gain medium, a dye gain medium, a crystal gain medium, a solid phase gain medium, or a semi-conductor laser gain medium.

In some embodiments, the rare-earth doped crystal comprises at least one Nd-doped host material such as Nd:YAG, Nd:YAP, and/or Nd:GdVO4. In alternative embodiments, the gain medium comprises other rare-earth or transition metal dopants, such as Er, Cr, Ho, Yb, Tm. Other suitable host materials may be glass or crystal materials such as KGW, YVO4, YLF, Forsterite, LiCAF, ZBLAN, or other fluoride or silica glasses. Other choices of gain media and host materials are known to the skilled person, e.g. for use at other wavelengths. See for example: W. Koechner, "Solid-State Laser Engineering", Sixth Edition, Springer Inc., 2006.

In some embodiments, the first laser resonator comprises at least one additional first gain medium and/or the second laser resonator comprises at least one additional second gain medium. In this way, advantages of different gain media may be combined within a single laser resonator.

Each laser source may comprise further optical components, such as a lens, a mirror, or other passive or active optical components, e.g. for shaping the optical field. In particular, the first laser resonator may comprise a first reflective element and a partly reflective first output coupler. Similarly, the second laser resonator may comprise a second reflective element and a partly reflective second output coupler. In some embodiments, the first reflective element comprises a mirror and/or the second reflective element comprises a mirror. Thus, an efficient laser resonator may be achieved, since a wide range of suitable mirrors are available to the skilled person. The mirror may be flat, convex, or concave, depending on e.g. the requirement for beam focusing, to overcome high peak powers, etc. In some embodiments, the first reflective element and/or the second reflective element is/are a grating, such as a fiber Bragg grating or a bulk grating.

The first gain medium may be configured for generating the first optical field along a first optical axis, e.g. as defined by the first laser resonator. The second laser source may be configured for generating the second optical field along a second optical axis, e.g. as defined by the second laser resonator. The at least one nonlinear medium may be configured for generating at least the third optical field along a third optical axis. An optical axis is here to be understood as an imaginary line that defines the path along which light propagates through the system. The axis may be deflected by, e.g. a mirror or other optical components. In some embodiments, the first laser resonator and the second laser resonator are arranged to have substantially overlapping optical axes in a common section over at least a part of a length of the first laser resonator and a part of a length of the second laser resonator, and wherein the first output coupler and the second output coupler are provided as a common output coupler. In this way, a compact system may be achieved, since one or more optical components may be shared between the two laser resonators.

In some embodiments, the first and second optical fields propagate through the nonlinear medium substantially parallel, i.e. such that, in the nonlinear medium, the first optical axis is parallel with, e.g. even coincides with, the second optical axis. Accordingly, the third optical axis may be parallel to, e.g. coincide with, the first and second optical axes at an output of the nonlinear medium. The first, second and third optical fields may thus conveniently be coupled into a radiation delivery device and directed to a well-defined target area. Moreover, this way an efficient conversion process is provided in the nonlinear medium.

For instance, the first output coupler may be a first mirror having a reflectance at the first wavelength of at least about 60%, such as at least about 65%, at least about 70%, at least about 75%, or at least about 80%, at least about 85%, or at least about 90%, or even at least about 95%. Similarly, the second output coupler may be a second mirror having a reflectance at the second wavelength of at least about 60%, such as at least about 65%, at least about 70%, at least about 75%, or at least about 80%, at least about 85%, or at least about 90%, or even at least about 95%. Similarly, a common output coupler may have such reflectance at each of the first and second wavelengths. Such mirrors are readily created by known arts, and may for example be obtained by coating non-absorbing, transparent substrates with multiple layers of dielectric materials such as fluorides and oxides Each of the first and second optical fields may have the same or different wavelengths. In some embodiments, one of the first and second laser sources is adapted for lasing with a first wavelength in the range from about 1020 nm to about 1080 nm, e.g. at 1064 nm, and the other one of the first and second laser sources is adapted for lasing with a second wavelength in the range from about 1300 nm to about 1350 nm, e.g. 1319 nm. Light within these wavelength ranges is particularly useful in treatments of various skin conditions. Wavelength of an optical field is throughout this document to be understood as the vacuum wavelength of the field.

In some embodiments, the nonlinear medium comprises at least one nonlinear crystal. In an alternative embodiment, the nonlinear medium comprises two, three, or more nonlinear crystals. In this way, problems such as back-conversion of the first optical field back into the first optical field and/or second optical field may be mitigated. In alternative embodiments, the nonlinear medium comprises a highly nonlinear fiber.

In some embodiments, the nonlinear crystal is chosen from LBO, BBO, KTP, BiBO periodically poled (PP) LN, or LT. These choices of nonlinear crystals are suitable for generation of light in the visible range, e.g. yellow light from infrared light.

The nonlinear interaction may be a sum-frequency-generation (SFG), Difference Frequency Generation (DFG) or second harmonic generation (SHG). In some embodiments, the nonlinear medium is configured to generate the third optical field by sum frequency generation or difference frequency generation from the first optical field and the second optical field, in particular where the first and second optical fields have different wavelengths. In this way, the third optical field may conveniently be generated from the first and second optical fields. Furthermore, this choice of nonlinear process may alleviate difficulties in obtaining laser light at shorter wavelengths, e.g. within the visible range, by generating this light from light at longer wavelengths, e.g. in the infrared range. In some embodiments, the third wavelength is between 570 nm and 620 nm, e.g. 589 nm.

In some embodiments, the medical laser system comprises at least one optical pump source for optically pumping the first gain medium and/or the second gain medium. In some embodiments, the medical laser system comprises at least one first optical pump source for pumping the first gain medium and at least one second optical pump source for pumping the second gain medium. In this way, a simple system may be achieved, wherein control of the optical power in the first optical field and the second optical field may be individually controlled by adjusting the power of the first pump source or the second pump source, respectively.

In some embodiments, the first gain medium is pumped substantially along the first optical axis and/or the second gain medium is pumped substantially along the second optical axis. End-pumping the gain media in this way is generally more pump efficient than pumping, e.g. normal to the optical axis. In alternative embodiments, the first gain medium and/or the second gain medium is side-pumped.

In some embodiments, the or each pump source comprises one or more laser diodes. Such diodes are both inexpensive, mechanically robust, and are practically maintenance free. In particular, in some embodiments, the one or more laser diodes of a pump source emit(s) laser light with a wavelength in the range from about 800 nm to about 900 nm, such as from about 805 nm to about 815 nm or from about 880 nm to about 890 nm, or even about 808 nm or about 885 nm. In alternative embodiments, the medical laser system comprises two pump sources one or more laser diodes of a pump source emit(s) laser light with a different wavelength, such as between 900 nm and 1000 nm.

In some embodiments, the medical laser system comprises two pump sources emitting laser light at respective wavelengths, e.g. such that the first and second gain media are pumped at respective wavelengths.

Embodiments of the medical laser system disclosed herein are particularly, though not exclusively, suitable as a dermatological laser system, e.g. for cosmetic skin treatment. Accordingly, in some embodiments, the medical laser system is configured for cosmetic skin treatment, such as for the purely cosmetic treatment of wrinkles or fine lines in skin, removal of freckles, etc. In some embodiments, the cosmetic treatment is photo rejuvenation of skin. To this end, in some embodiments, the medical laser system is configured for irradiating a user-selectable target skin area with laser light having one, two, three or more distinct wavelengths simultaneously or in succession via a hand-held radiation delivery device. By delivering more than one wavelength simultaneously or in rapid succession, an improved treatment may be achieved.

In some embodiments, the medical laser system is configured to irradiate the target skin area by one or more bursts of pulsed laser light, each burst comprising a pulse train of laser pulses, the laser light having one or more wavelength components suitable for heating constituents in the skin.

In some embodiments, the third wavelength is chosen from the range from about 510 nm to about 620 nm, such as from about 510 nm to about 600 nm. In some embodiments one or both of the first and second wavelengths are chosen from the range from about 1020 nm to about 1080 nm and/or from the range from about 1300 nm to about 1350 nm. In other embodiments, other wavelengths may be used.

In some embodiments, the third wavelength is chosen from the range from about 570 nm to about 600 nm, one of the first and second wavelengths is chosen from the range from about 1020 nm to about 1080 nm, and the other one of the first and second wavelengths is chosen from the range from about 1300 nm to about 1350 nm, such as about 589 nm, about 1064 nm, and about 1319 nm, respectively, or such as about 593 nm, about 1064 nm, and about 1341 nm, respectively, or even such as about 598 nm, about 1079 nm, and about 1341 nm. These wavelengths may be used separately in treatment of various skin problems and have different ways of interacting with the skin layers due to different absorption/penetration of the wavelengths into the layers. For instance, light with wavelengths in the range from about 570 nm to about 600 nm may be used for treatment of minor vessels, red discoloration of skin, hyperpigmentation, and to stimulate collagen growth. Light with wavelengths of about 1064 nm or about 1079 nm has a very good penetration due to the low absorption in melanin, hemoglobin and water and may be used to stimulate collagen growth and treat deeper lying vessels. Light with wavelengths of about 1319 nm or 1350 nm has a good penetration, but higher absorption in water and fatty tissue than, e.g. 1064 nm or 1079 nm light, and may be used to improve skin elasticity and to stimulate collagen growth. A laser system capable of rapidly switching between multiple wavelengths allows reduction of the treatment time.

In other embodiments, the first wavelength is chosen from the range from about 900 nm to about 980 nm, e.g. the first wavelength may be chosen to be 946 nm. The second wavelength may be chosen from the range from about 1350 nm to about 1650 nm or from the range from about 1500 nm to about 1600 nm. e.g. e.g. the second wavelength may be chosen to be 1550 nm. For example, the first wavelength may be chosen to be 1550 nm, e.g. using an Er:glass gain medium, and the second wavelength may be chosen to be 946 nm, e.g. using an Nd(:YAG) gain medium, thus resulting in a third wavelength of about 587 nm. Alternatively, an Er:fibre or Cr+4 such as Cr:YAG gain medium or other suitable gain medium may be used to provide a first wavelength in the range 1350 nm-1650 nm, and an Nd:xxx gain medium or other suitable gain medium may be used to provide a second wavelength in the range 900 nm-950 nm (e.g. 914 nm or 946 nm).

In yet other embodiments, the first wavelength is chosen from the range from about 1100 nm to about 1370 nm, such as between 1285 nm and 1370 nm. The second wavelength may be chosen from the range from about 1030 nm to about 1080 nm, e.g. 1064 nm or 1030 nm or even 1080 nm. For example, a Cr+4 such as a Cr:Forsterite (tunable) medium or another suitable gain medium may be used to provide a wavelength in the range 1100 nm-1370 nm and an Nd-doped gain medium or other suitable medium may be used to provide a wavelength in the range 1030 nm-1080 nm.

In some embodiments, the first and second wavelengths are the same and the first and second optical fields have different polarization states, e.g. vertical and horizontal. For example, in some embodiments, the first and second wavelengths are in the range of about 1020 nm to about 1080 nm, such as 1064 nm. The third wavelength may be between about 510 nm and about 540 nm, such as 532 nm.

In some embodiments, the medical laser system is operable to feed more than two optical fields into at least one nonlinear medium, e.g. a first, a second and a fourth optical field. The fourth optical field may have a fourth wavelength which may be the same wavelength as one or both of the first and second wavelengths or a wavelength different from the first and second wavelengths. The fourth optical field may be in the form of a fourth pulse train of laser pulses along a fourth optical axis. The fourth optical axis may, in the nonlinear medium, be parallel with, e.g. coincide with, the first and/or the second optical axis.

To this end the laser system may include a further laser source, e.g. including a laser resonator, a further gain medium and a further Q-switch, as described in connection with the first or second laser source. The further laser source may be pumped by a further pump source. The further Q-switch may be controlled by the control signal. To this end, the control signal may control operation of the further Q-switch by a further adjustable delay.

The control circuit may thus be configured to control the relative timing of the pulses of the first, second and fourth pulse train (and optionally of yet further pulse trains). When the laser pulses of the first and fourth pulse trains temporally overlap in the at least one nonlinear medium, a fifth optical field may be generated by a nonlinear interaction between the first and the fourth optical fields. Similarly, alternatively or additionally, when the laser pulses of the second and fourth pulse trains temporally overlap in the at least one nonlinear medium, a sixth optical field may be generated by a nonlinear interaction between the second and the fourth optical fields. Accordingly, the control circuit may selectively control which optical field(s) is/are included in the output radiation of the laser system by controlling relative delays between the respective pulse trains.

In one embodiment, the at least one nonlinear medium comprises:
  a first nonlinear medium operable to generate the third optical field from the first and second optical fields; and
  a second nonlinear medium operable to generate the fifth optical field from the first and second optical fields;

The first and second nonlinear media may be arranged such that the first, second and fourth optical fields are fed through the first nonlinear medium and then through the second nonlinear medium, together with any third optical field generated by the first nonlinear medium. When the laser pulses of the first and second optical fields overlap in the first nonlinear medium, the output radiation includes the third optical field. When the laser pulses of the first and the fourth optical fields overlap in the second nonlinear medium, the output radiation includes the fifths optical field. In this example, the relative timing of the second and fourth pulse trains may be configured such that they do not overlap in the first or second nonlinear media. However, in other examples, their relative timing may also be adjustable so as to cause their laser pulses to selectively overlap in at least one of the nonlinear media.

Generally, embodiments of the medical laser system disclosed herein provide an improved treatment, while advantages such as compactness, ease of use, and/or economic benefits of the laser system are maintained.

In some embodiments, the medical laser system is configured to irradiate the target skin area in bursts of pulsed laser light, each burst having a duration in a range from about 0.5 ms to about 1000 ms, such as from about 0.5 ms to about 900 ms, such as from about 0.5 ms to about 800 ms, such as from about 0.5 ms to about 600 ms, such as from about 0.5 ms to about 400 ms, such as from about 0.5 ms to about 300 ms, such as from about 10 ms to about 200 ms, or even from about 20 ms to about 100 ms, or from about 10 ms to about 40 ms, or from about 0.5 ms to about 40 ms, such as from about 1 ms to about 20 ms, such as from about 0.5 ms to about 4 ms. The burst repetition rate may vary considerably and may in some embodiments be selected in the range from 0.1 Hz to 20 Hz, such as from 0.1 Hz to 10 Hz, such as from 0.1 Hz to 5 Hz. In some embodiments, even lower or higher repetition rates may be desirable. In some embodiments, the pulse repetition rate between the individual pulses of a burst may be selected in the range from 0.5 Hz to 500 kHz, such from 1 Hz to 500 kHz, such as from 5 Hz to 500 kHz, such as from 10 Hz to 200 kHz, such as from 1 kHz to 100 kHz, e.g. from 5 kHz to 30 kHz, such as from 10 kHz to 20 kHz. It will be appreciated that the choice of pulse repetition rate may depend on the components of the laser system. The pulse repetition rate may be the same for all optical fields. However, in some embodiments the pulse repetition rate may vary from field to field and/or over time.

In some embodiments, the medical laser system is configured to deliver a total radiant exposure of the target area in a range of about 15 $J/cm^2$ to about 150 $J/cm^2$ for each distinct wavelength. In some embodiments, the medical laser system is configured to deliver a total radiant exposure of the target area in a range of about 5 $J/cm^2$ to about 100 $J/cm^2$ per distinct wavelength, for example in the range from about 5 $J/cm^2$ to about 50 $J/cm^2$ for each distinct wavelength.

In some embodiments, the hand-held radiation delivery device is configured to scan the beam in a scanning pattern of individual target skin areas covering a treatment area. The scanning pattern may be pre-set or selectable among a number of pre-programmed patterns, or even be directly programmable, e.g. by a user of the laser system. In some embodiments, the scanning pattern is a rectangular pattern of individual target skin areas "spots", with a pattern consisting of 3 to 15 spots in each direction, such as for example a 5×5 pattern, or for example a 6×6 pattern, or for example a 7×7 pattern, or for example a pattern with variable spot density in the range of 3-to-15 by 3-to-15 spots.

In some embodiments, the individual target skin areas of said scanning pattern are addressed with alternating wavelengths, e.g. such that two neighboring target skin areas being irradiated with different wavelengths when irradiated in a direct sequence immediately after each other. Avoiding exposure on two neighboring target skin areas in sequence, or at least avoiding exposure with the same wavelength, reduces risk for general damages to the treatment area. In some embodiments, a dwell time at said individual target skin area positions is in the range from about 0.5 ms to about 100 ms, such as between 0.5 ms and 10 ms, e.g. between 0.5 ms and 4 ms.

In some embodiments, the scanned treatment area substantially forms a rectangle with an extent along each side in the range from about 3 mm to about 10 mm, such as for example a 3 mm-by-3 mm area, or for example a 5 mm-by-5 mm area, or for example a 5 mm-by-10 mm area, or even for example a 10 mm-by-10 mm area.

In some embodiments, a size, such as a diameter or a greatest extent of the target skin area is selected to be in the range from about 0.8 mm to about 5.0 mm, such as about 1.0 mm, such as about 2.0 mm, such as about 3.0 mm, or even such as about 4.0 mm. The size of the target skin area may be defined by the spot size on the skin of the laser light, i.e. the irradiated spot on the skin.

As embodiments of the medical laser system described herein facilitate a fast switching and/or efficient control of the third optical field, they are particularly useful for a real-time automatic control the output of the medical laser system, e.g. based on measurements of the target area and/or the laser output. To this end, the laser system may include a sensor operable to detect or monitor an effect of the laser output on the target area. The control circuit may then be configured to control generation of the third optical field (in particular by adjusting the adjustable delay) responsive to the detected or monitored effect. Examples of the effect may be a temperature, a light intensity, or the like. In some embodiments, the sensor includes a camera configured to capture images of the target area during treatment, and the medical laser system may be configured to process one or more images captured by the camera so as to determine an effect of the laser output on the target area.

The present disclosure relates to different aspects, including the method described above and in the following, further methods, systems, devices and product means, each yielding one or more of the benefits and advantages described in connection with one or more of the other aspects, and each having one or more embodiments corresponding to the embodiments described in connection with one or more of the other aspects described herein and/or as disclosed in the appended claims.

In particular, another aspect disclosed herein relates to embodiments of a method for controlling a medical laser system, the medical laser system comprising:
  a first laser source comprising a first laser resonator, at least a first gain medium, and at least one first Q-switch configured to control a resonance quality of the first laser resonator;
  a second laser source;
  at least one nonlinear medium for generating a third optical field by a nonlinear interaction between the first optical field and the second optical field;
  a sensor configured to detect a property of at least one of the optical fields;
the method comprising:
  causing the first laser source to generate a first optical field along;

controlling the first Q-switch to cause the first laser resonator to generate the first optical field as a first pulse train of laser pulses;

causing the second laser source to generate a second optical field as a second pulse train of laser pulses;

receiving a sensor signal from the sensor, the sensor signal being indicative of a property of at least one of the first, second and third optical fields;

controlling the first Q-switch to cause the first laser resonator to generate the first optical field as a first pulse train of laser pulses;

controlling operation of the first Q-switch so as to adjust a relative timing of the laser pulses of the first pulse train and the laser pulses of the second pulse train responsive to the received sensor signal.

BRIEF DESCRIPTION OF THE DRAWINGS

The above and other aspects will be apparent and elucidated from the embodiments described in the following with reference to the drawing in which.

DETAILED DESCRIPTION

Figure 1:
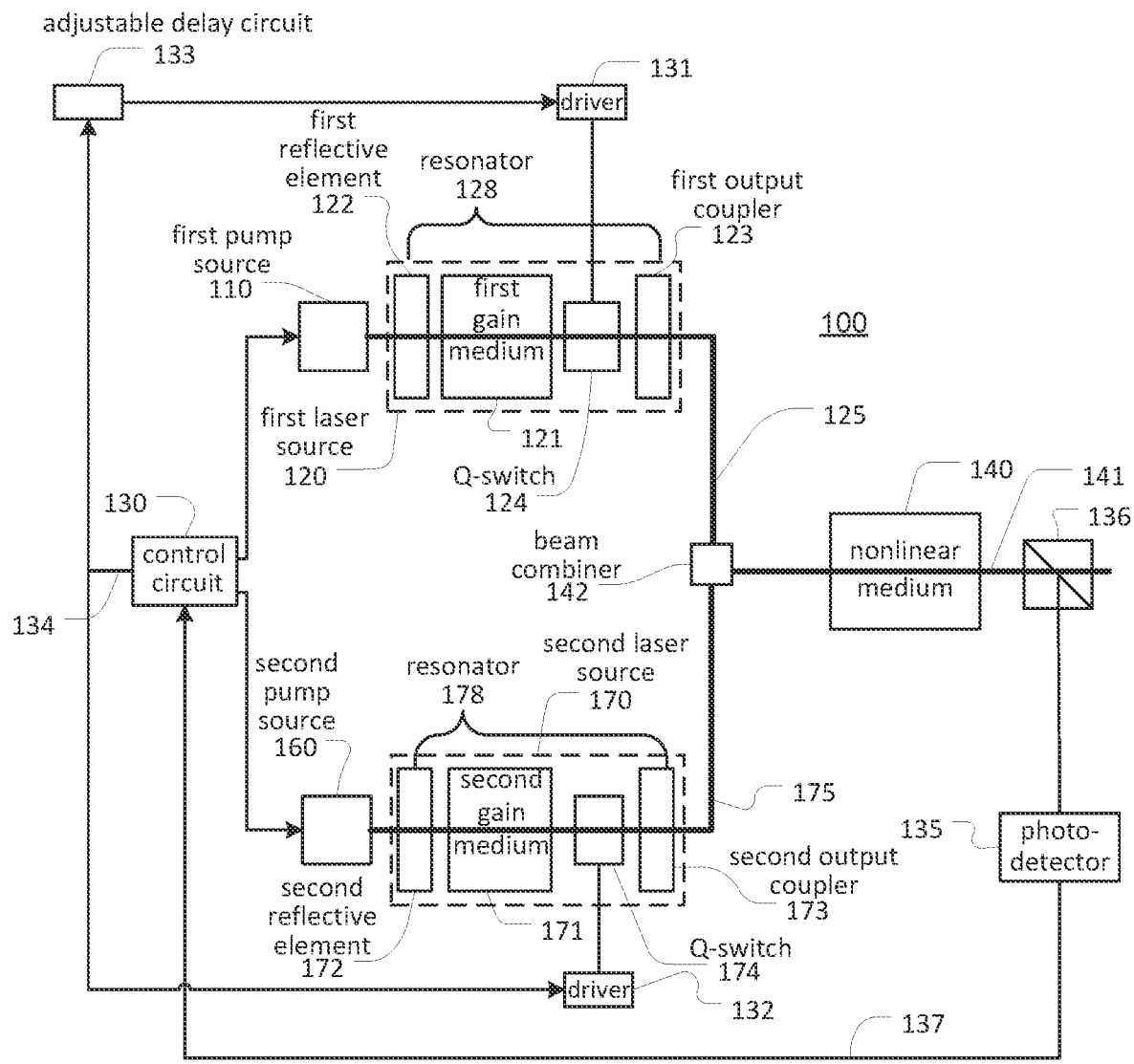
FIG. 1 schematically illustrates an embodiment of a medical laser system.

FIG. 1 schematically illustrates an embodiment of a medical laser system. The medical laser system, generally designated by reference numeral 100, comprises a first laser source 120 and a second laser source 170. Both the first laser source 120 and the second laser source 170 may be provided in the form of respective cavities or other resonators 128 and 178, respectively, for creating first and second optical fields, respectively.

The first laser source 120 includes a first gain medium 121 of an Neodymium (Nd) doped host material such as Nd:YAG, capable of emitting light at the first wavelength of 1064 nm. The first gain medium 121 is located inside the resonator 128 of the first laser source, on a first optical axis defined by the resonator 128. The laser resonator of the first laser source 120 is bounded on one side by a first reflective element 122, such as a mirror. The resonator 128 of the first laser source is bounded on a second side by a partly reflective first output coupler 123 that is partly reflective to the first optical field so as to couple out parts of the circulating laser field. The first output coupler is partially reflective at the first wavelength of 1064 nm. For example, in certain embodiments the reflectance for light with a wavelength of about 1064 nm is at least about 60%, such as at least about 65% or at least about 70%, or even at least about 75% or at least about 80%. Such an output coupler may be provided as a mirror that is readily created by known arts, and is for example accomplished by coating non-absorbing, transparent substrates with multiple layers of dielectric materials such as fluorides and oxides. The first laser source outputs the first optical field 125 at the first wavelength along the first optical axis.

Similarly, the second laser source 170 includes a second gain medium 171 inside the second resonator 178, on a second optical axis 117 defined by the resonator 178 of the second laser source 170. The second gain medium comprises a Nd doped host material such as Nd:YAG, capable of emitting light at a second wavelength of 1319 nm. The resonator 178 of the second laser source 170 is bounded by a second reflective element 172 and a by partly reflective second output coupler 173 that is partly reflecting to the second optical field so as to couple out parts of the circulating laser field from the resonator of the second laser source. The second output coupler is partially reflective at the second wavelength of 1319 nm. For example, in certain embodiments, the reflectance of the second output coupler at about 1319 nm is at least about 85%, such as at least about 90%, or even at least about 95%. The second laser source outputs the second optical field 175 at the second wavelength along the second optical axis.

While shown as completely separate cavities in FIG. 1, the resonators of first laser source 120 and the second laser source 170 may share a part of the cavity referred to as the common section. Within the common section, the first optical axis and the second optical axis may substantially be coinciding or parallel.

Other examples of suitable gain materials include Nd:YAP capable of lasing at about 1079 nm or at about 1341 nm, Nd:GdVO4 capable of lasing at about 1064 nm or at about 1341 nm, or Yb:YAG emitting at about 1030 nm. Yet further examples include crystal hosts such as YAG, forsterite, YAP, YVO4, LiCAF and KGW doped with active rare-earth or transition metal ions such as Nd, Er, Yb, Cr, and Ho. Optionally the host may be a silica glass, or fluoride glass. The first gain medium 121 and the second gain medium 171 are not required to be of the same kind, such as the first gain medium 121 being of Nd:YAG emitting at 1064 nm and the second gain medium being of Nd:YAP 171 emitting at 1341 nm. Other combinations may be suitable for particular uses to which the laser system 100 is being employed and will be readily apparent to those skilled in the art given the benefit of this disclosure.

Generally, in some embodiments, the wavelengths of the first and/or second optical fields are in the range 1000 nm-1250 nm, or 1150 nm-1200 nm, e.g. 1170 nm-1190 nm, e.g. 1178 nm or even 1020-1080 nm, e.g. 1064 nm. The third wavelength may be in the range 500 nm-625 nm, such as 575 nm-600 nm, such as 585 nm-595 nm, e.g. 589 nm, or even 510 nm-540 nm e.g. 532 nm.

The medical laser system comprises a first Q-switch 124 coupled to the first gain medium 121. When activated, the first active Q-switch alters the quality factor (Q) of resonance for the first gain medium at the first wavelength. The first Q-switch may be an acousto-optical modulator. The laser system further includes a first driver 131, e.g. an RF-generator, or an electro-optical modulator controlled by a high-voltage generator. The first driver is operable to activate the Q-switch in response to a received trigger signal.

Similarly, the medical laser system comprises a second Q-switch 174 coupled to the second gain medium 171. When activated, the second active Q-switch alters the quality factor (Q) of resonance for the second gain medium at the second wavelength. The second Q-switch may be an acousto-optical modulator. The laser system further includes a second driver 132, e.g. an RF-generator, or an electro-optical modulator controlled by a high-voltage generator. The second driver is operable to activate the Q-switch in response to a received trigger signal.

Alternatively, one of the Q-switches may be of passive type, comprising e.g. Cr:YAG, V:YAG and/or Cr:Forsterite.

The first optical field and the second optical field are combined to have substantially common optical axes. This may be accomplished by utilizing a beam combiner 142, such as a dichroic mirror which is essentially transparent for the first or the second wavelength while essentially reflecting for the other wavelength. For example, the mirror is essentially transparent for light with a wavelength of about 1064 nm, while reflectance for light with a wavelength of about 1319 nm is at least about 95%, such as at least about 99%. In this fashion the two beams may be overlaid. Another example of a beam combiner is a dispersing prism. Other examples of beam combiners are reflection gratings and transmission gratings.

The laser system comprises a nonlinear medium 140 for sum frequency generation conversion of the first optical field and the second optical field into the third optical field. The nonlinear medium receives the combined first and second optical fields from the beam combiner 142. The nonlinear medium 140 for sum frequency generation is here implemented by an LBO crystal. The LBO may be arranged for non-critical phase matching. A typical length of the LBO crystal is in the range from about 10 mm to about 50 mm, such as in the range from about 15 mm to about 25 mm, or even about 20 mm. In other embodiments other types of nonlinear media may be utilized and/or other nonlinear processes may be employed.

The laser system comprises a first pump source 110 for optically pumping the resonator of first laser source, and a second pump source 160 for optically pumping the resonator of the second laser source. The pump sources may, for instance, be fiber-coupled laser diodes. Typical pump wavelengths may be about 808 nm or about 885 nm.

The laser system further comprises a control circuit 130 for controlling the various components of the laser system. In particular, the control circuit is operable to control operation of the pump sources and to generate a trigger signal for triggering the Q-switches. The control circuit may at least in part be implemented by a suitable microprocessor, as a phase-locked loop component, an FPGA, and CPLD and/or the like. The control circuit may be implemented as a single functional block or as multiple functional blocks. In particular, the control circuit creates a trigger signal 134 which is forwarded to the first driver 131 via an adjustable delay circuit 133 and to the second driver 132. Of course, alternatively, the delay circuit may be positioned in the signal path of the trigger signal from the control signal to the second driver. Yet alternatively both trigger signals may be delayed by respective adjustable delays. The drivers 131 and 132 control the respective Q-switches to alternately increase and decrease the quality factor of the respective gain media. Accordingly, each laser source outputs a sequence (or train) of short laser pulses. The respective pulse trains reach the nonlinear medium 140. The control circuit 130 may control the adjustable delay 133 such that the laser pulses from the first laser source reach the nonlinear medium at the same time as corresponding laser pulses from the second laser source, i.e. such that the laser pulses from the first laser source coincide (or at least overlap temporally) with respective pulses from the second laser source in the nonlinear medium. Accordingly, the laser pulses from the first and second laser source can interact in the non-linear medium so as to generate laser pulses of the third optical field. Accordingly, the control circuit 130 can control the adjustable delay 133 such that the laser light 141 output by the non-linear medium 140 includes light of the third optical field resulting from the nonlinear process. The amount of light of the third optical field depends on the operation conditions of the nonlinear medium as on the amount of temporal overlap of the incoming pulses from the first and second laser sources. In any event, the output 141 from the non-linear medium may also include a certain amount of light at the first and/or second wavelength.

Alternatively, the control circuit 130 may control the adjustable delay 133 such that, in the nonlinear medium, the pulses from the first laser source coincide with gaps (pauses) between pulses from the second laser sources, i.e. such that the pulses from the first and second laser sources do not overlap temporally in the nonlinear medium. Accordingly, with such a setting of the adjustable delay, no efficient interaction between the first and second optical fields can occur in the nonlinear medium and the output 141 from the nonlinear medium will only include respective pulse trains at the first and second wavelengths.

If desired, the first and/or second wavelengths may be filtered out from the output 141 from the nonlinear medium, e.g. by an output selector as described below. This may be done permanently or selectively, e.g. responsive to a wavelength selection signal.

The control circuit 130 may thus control the relative timing of the pulses from the first and second laser source by adjusting the adjustable delay 133. As the appropriate delay that causes the pulses from the first and second laser sources to coincide may change over time, e.g. due to drift or other instabilities of the various components of the laser system, the control circuit should preferably continuously or at least intermittently adapt the adjustable delay. To this end, the control circuit may receive a signal indicative of relative timing of the pulses in the non-linear medium and adapt the adjustable delay based on the received signal.

To this end, the embodiment of FIG. 1 includes a beam splitter 136 which receives the output 135 from the nonlinear medium 140 and which directs a minor portion of the output 141 at the third wavelength (or otherwise a minor portion of the third optical field output by the nonlinear medium) towards a photodetector 135. The output from the photodetector is fed to the control circuit 130 as a signal 137 that is indicative of the intensity of the third optical field, i.e. indicative of the efficiency of the nonlinear process in the nonlinear medium. The control circuit may thus adjust the delay 133 so as to maximize the detected intensity of the third optical field. It will be appreciated that the laser system may be configured such that the photodetector 135 receives and detects the first and/or second wavelength and the control circuit may then be configured to adjust the delay 133 so as to minimize the content of the first and/or second wavelength in the output 141 from the nonlinear medium 140.

As will be described in greater detail below, the control circuit may also operate as an exposure control device, as the control circuit may selectively desynchronize the pulses from the first and second laser sources so as to prevent the third optical field from being generated in the nonlinear medium. Accordingly, the control device may be operable to selectively turn the third optical field on and off. In some embodiments, the control circuit 130 may thus selectively control generation of the third optical field so as to generate short bursts of laser light at the third wavelength, e.g. burst including a pulse train of one or more pulses. In this manner, very short bursts of light may be created, in particular bursts shorter than 10 ms and even bursts of 1 ms or less. Moreover, the control circuit 130 may turn the third optical field on or off responsive to a corresponding command, e.g. responsive to an operator of the system initiating operation at the third wavelength.

Figure 2:
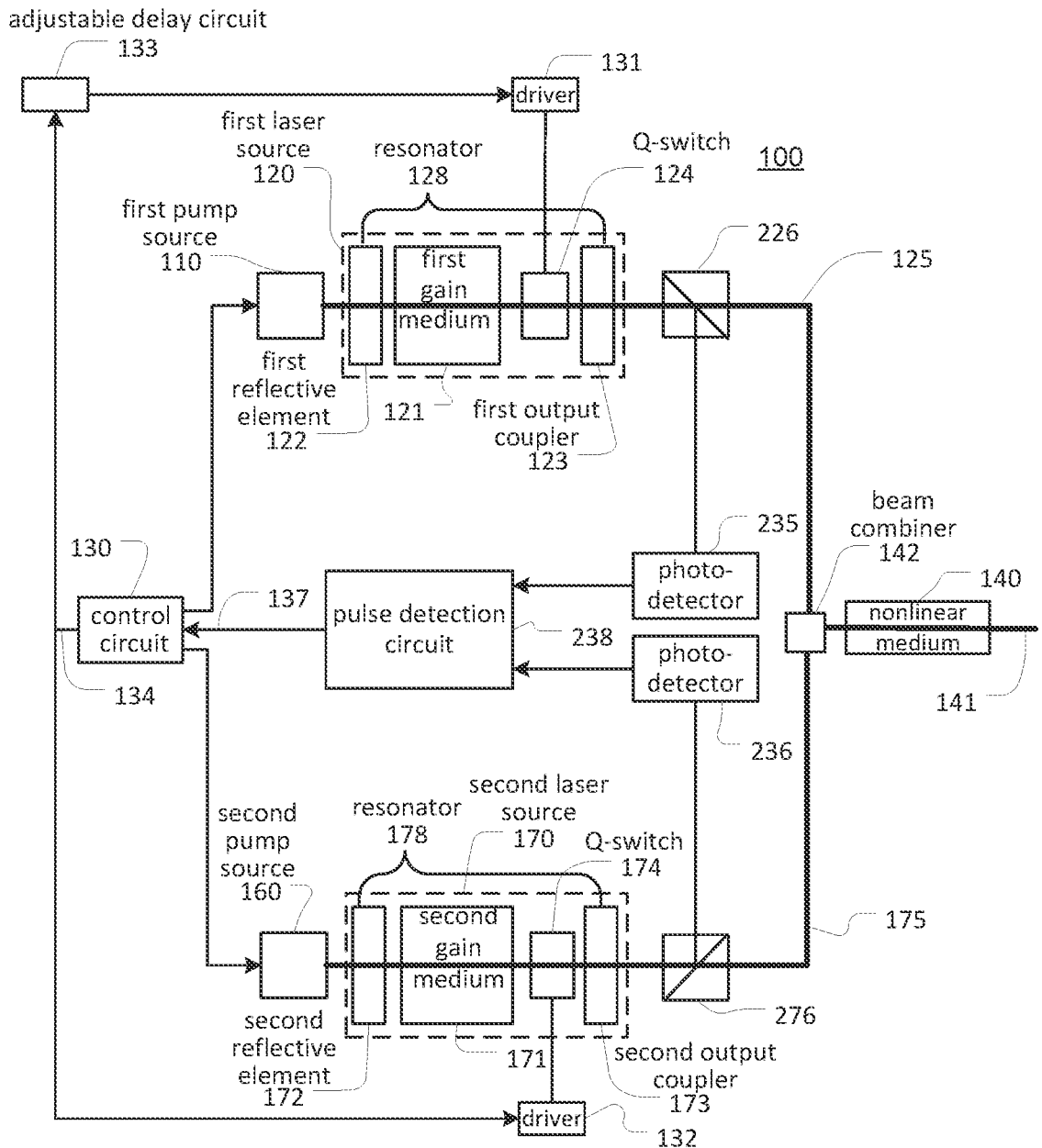
FIG. 2 schematically illustrates another embodiment of a medical laser system.

FIG. 2 schematically illustrates another embodiment of a medical laser system. The medical laser system of FIG. 2 is similar to the embodiment shown in FIG. 1 in that it comprises a first pump source 110, a second pump source 160, a first laser source 120, a second laser source 170, a beam combiner 142, a nonlinear medium 140, drivers 131 and 132 for driving respective Q-switches 124 and 174 of the first and second laser sources, respectively, an adjustable delay circuit 133 and a control circuit 130, all as described in connection with FIG. 1.

In particular, as was described in detail with reference to FIG. 1, the control circuit 130 controls the adjustable delay 133 so as to control the relative timing of the laser pulses from the first laser source and the second laser source. Specifically, the control circuit may be operable to selectively turn generation of the third optical field on or off. To this end the control circuit receives a signal 137 based on which the control circuit determines the appropriate delay setting that causes the pulses from the first laser source to temporally overlap with corresponding pulses from the second laser source.

In the present embodiment, the signal 137 is created based on measured outputs of the respective first and second laser sources. To this end, the medical laser system of the present embodiment comprises a first beam splitter 226 that directs a minor portion of the first optical field 125 towards a first photodetector 235. Similarly, the medical laser system of the present embodiment comprises a second beam splitter 276 that directs a minor portion of the second optical field 175 towards a second photodetector 236. The photodetectors 235 and 236 forward their respective detection signals to a pulse detection circuit 238. The pulse detection circuit detects the laser pulses of the pulse trains of the first and second optical fields, respectively, and determines the time lag between the respective pulses. The pulse detection circuit then forwards a signal 137 to the control circuit 130 indicative of the detected time lag. When the control circuit 130 is to cause generation of the third optical field, the control circuit may thus select the adjustable delay 133 such that the time lag is minimized.

It is an advantage of this embodiment that the signal 137 indicative of the time lag can be produced independently of the generation of the third optical field and, in particular, even when the time lag is currently such that no third optical field is created in the optical medium. Accordingly, the control circuit 130 may determine an accurate value of the optimal delay for creation of the third optical field even during time periods when the third optical field is turned off, i.e. during periods where the control circuit controls the adjustable delay 133 such that no third optical field is created, e.g. during periods where the operator has selected treatment with only one or both of the first and second wavelengths rather than the third wavelength. This embodiment thus allows a fast switching on of the third optical field even in situations when the corresponding optimal delay for the generation of the third optical field has changed during the off period, e.g. due to thermal drift or the like.

Figure 3:
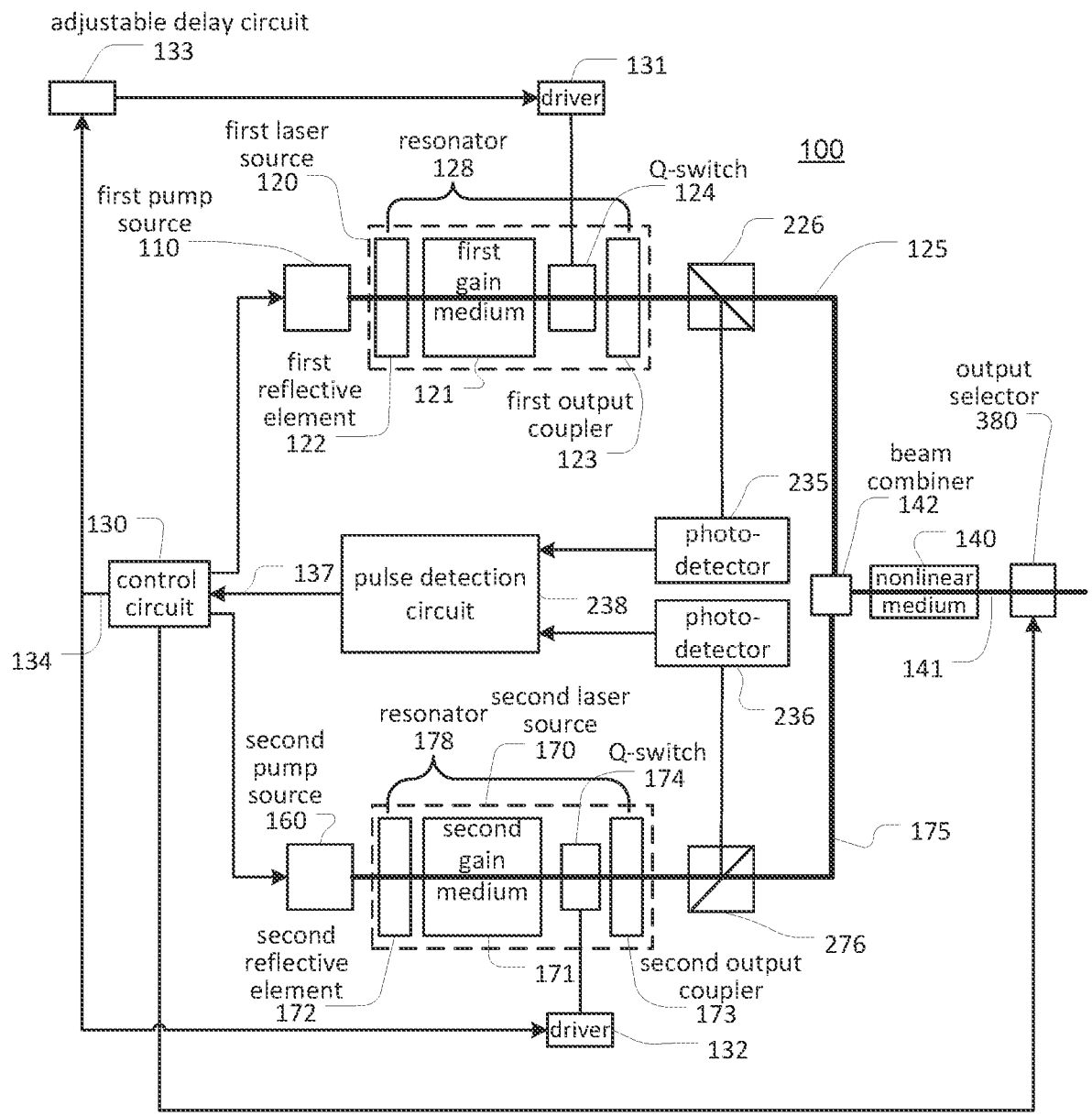
FIG. 3 schematically illustrates yet another embodiment of a medical laser system.

FIG. 3 schematically illustrates yet another embodiment of a medical laser system. The medical laser system of FIG. 3 corresponds to the embodiment shown in FIG. 2 in that it comprises a first pump source 110, a second pump source 160, a first laser source 120, a second laser source 170, a beam combiner 142, a nonlinear medium 140, drivers 131 and 132 for driving respective Q-switches 124 and 174 of the first and second laser sources, respectively, an adjustable delay circuit 133, first and second beam splitters 226, 276, first and second photodetectors 235 and 236, a pulse detection circuit 238 and a control circuit 130, all as described in connection with FIG. 2.

The embodiment of FIG. 3 differs from the embodiment of FIG. 2 in that the medical laser system of FIG. 3 further comprises an output selector 380 positioned in the beam path of the output 141 from the nonlinear medium 140. The output selector 380 is operatively coupled to the control circuit 130 such that the control circuit controls operation of the output selector 380.

The output selector 380 may be implemented as a mirror selector holding a number of selection mirrors. The mirror selector is configured, responsive to a control signal from control circuit 130 to position a chosen selection mirror to intersect the first optical axis, second optical axis and third optical axis. At the output of the nonlinear medium, the first, second and third optical axes may substantially coincide. The mirror selector may comprise a wheel with slots around the circumference, into which the selection mirrors are mounted. Alternatively, it may comprise a linear stage with slots, into which the selection mirrors are mounted. Yet alternatively, it may comprise an axle with radially mounted arms or vanes appropriate for holding mirrors. The mirror selector may comprise an electrical stepper motor, a linear motor, or an electrical motor. To assist exact positioning of the mirror selector a disc with slots in combination with means for optically reading the disc position to establish the mirror selector position may e.g. be used. Optionally an electronic counter may be used for reading the mirror selector position. Other examples of mirror selectors are readily apparent to those skilled in the art given the benefit of this disclosure.

It will be appreciated that the complexity of the output selector, e.g. the number of mirrors and different selectable positions, is simplified when the third optical field can be turned on and off by the control circuit adjusting the relative timing of the laser pulses in the nonlinear medium. Moreover, the selective inclusion of the third wavelength in the output of the laser system may be performed very fast by embodiments of the laser system disclosed herein.

For example, the selection mirrors may be chosen as to enable control of which of the optical fields emitted from the laser system is/are available at an output port. For instance, the optical fields transmitted through the selection mirrors are routed to the output port, while the optical fields reflected are passed to a beam dump. Alternatively, the reflected optical fields are routed to the output port of the laser system while the transmitted optical fields are passed to the beam dump. In another alternative both the reflected and transmitted optical fields are used as output from the laser system 100, e.g. the reflected optical field being output from a primary output port, and the reflected optical field being output from a secondary output port.

In an example, where the transmitted fields are used as output from the laser system a first selection mirror may have a transmittance at the third wavelength (e.g. a wavelength of about 589 nm) of at least about 90%, such as at least about 95%, or even about 99.5%, and may have a reflectance at the first wavelength (e.g. a wavelength of about 1064 nm) of at least about 50%, such as at least about 75%, such as at least about 90%, or even at least about 99%. Finally, the first selection mirror may have a reflectance at the second wavelength (e.g. a wavelength of about 1319 nm) of at least about 50%, such as at least about 75%, such as at least about 90%, or even at least about 99%.

A second selection mirror may have a transmittance at the third and first wavelengths of at least about 90%, such as at least about 95%, or even about 99.5%, and may have a reflectance at the second wavelength of at least about 50%, such as at least about 75%, such as at least about 90%, or even at least about 99%.

Finally, a third selection mirror may have a transmittance at the third and second wavelengths of at least about 90%, such as at least about 95%, or even about 99.5%, and may have a reflectance at the first wavelength of at least about 50%, such as at least about 75%, such as at least about 90%, or even at least about 99%.

It will be appreciated that an output selector 380 may also be implemented in the medical laser system of FIG. 1 e.g. upstream or downstream of the beam splitter 136 of FIG. 1.

It will further be appreciated that embodiments of the laser system may include additional or alternative components. For example, the medical laser system may include a hand-held radiation deliver device, e.g. as described in connection with FIG. 5 below. Some examples of a medical laser system may include a mechanical or other type of shutter or exposure control element. It will further be understood that some embodiments of the medical laser system may include further optical elements such as lenses, beam redirecting elements, filters, etc. all conventional in the art.

Figure 4:
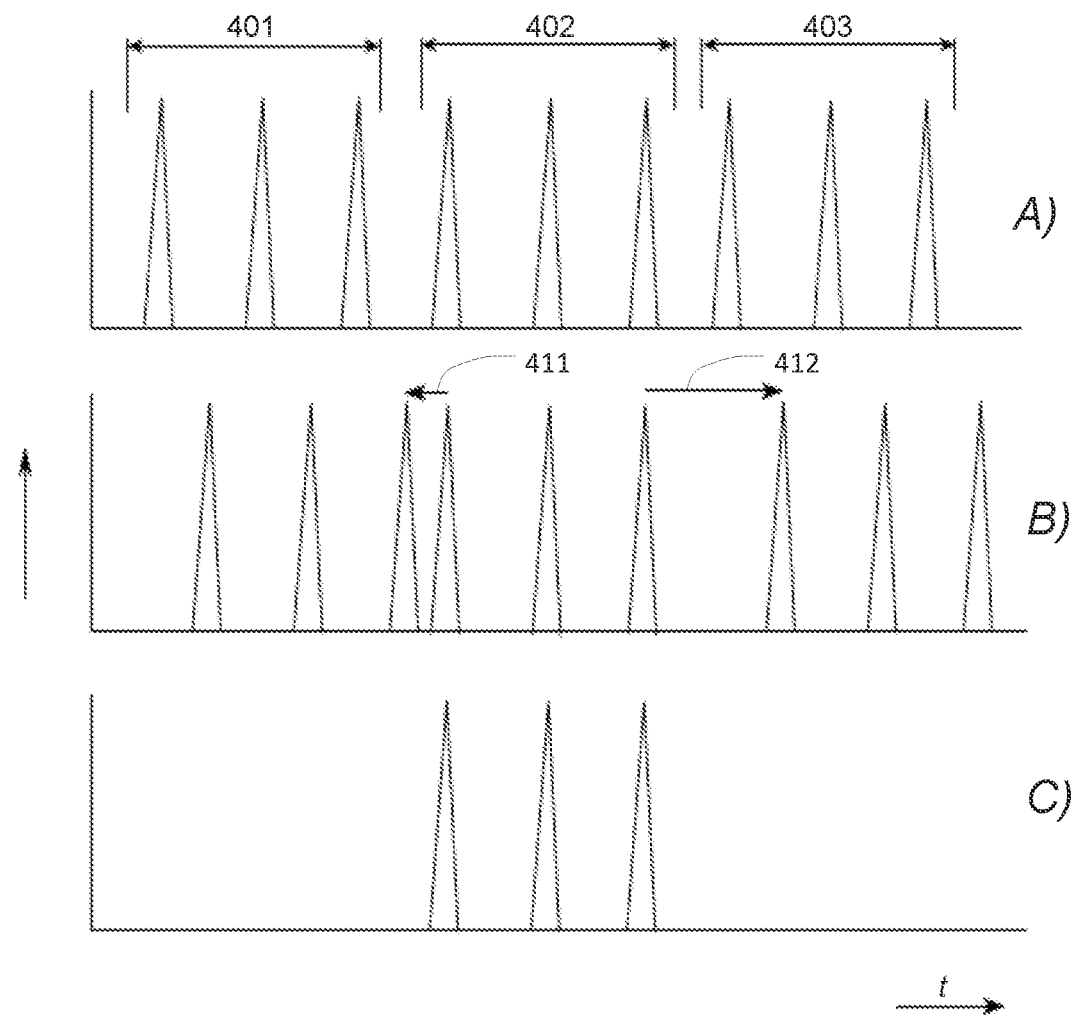
FIG. 4 schematically illustrates the control of the relative timing of laser pulses in the nonlinear medium.

FIG. 4 schematically illustrates the control of the relative timing of laser pulses in the nonlinear medium in the embodiments shown in any one of FIGS. 1-3.

In particular, FIG. 4A) shows an example of a pulse train from the second laser source, FIG. 4 B) shows an example of a pulse train from the first laser source and FIG. 4 C) shows an example of a corresponding pulse train of laser pulses of the third optical field generated by the nonlinear medium. As can be seen from FIG. 4A), the pulses emitted by the second laser source are substantially equidistant in time, as controlled by a master trigger signal to the second driver driving the second Q-switch. Similarly, FIG. 4 B) illustrates that, during periods where the adjustable delay is kept constant, the pulses emitted by the first laser source are also substantially equidistant, as controlled by the delayed master trigger signal to the first driver driving the first Q-switch. The relative timing between the pulses from the first and second laser sources is controlled by the magnitude of the adjustable delay.

Specifically, in the example of FIG. 4, during an initial period 410, the relative timing is selected such that the pulses from the first and second laser source due not coincide (and do not even overlap) in time. Accordingly, as there are no coinciding first and second optical fields in the nonlinear medium, they cannot interact with each other in the nonlinear medium. Consequently, no laser light of the third optical field is created during period 410, as illustrated in FIG. 4 C).

At point 411, the adjustable delay is changed, in this example, reduced. The change in the adjustable delay is selected such that, during the subsequent period 402, the pulses from the first and second laser source do indeed coincide (or at least substantially overlap in time). Accordingly, the nonlinear interaction between the first and second optical fields can take place in the nonlinear medium, resulting in the generation of corresponding laser pulses of the third optical field, as illustrated in FIG. 4 C).

At subsequent point 412, the adjustable delay is changed again (in this example increased), so as to again cause the laser pulses from the first and second laser source to not temporally overlap in the nonlinear medium. Hence, during the subsequent period 403, no laser pulses of the third optical field are generated, as illustrated in FIG. 4 c).

As is apparent from FIG. 4, by selectively adjusting the delay between the laser pulses from the first and second laser sources, respectively, the third optical field can be selectively turned on or off. Accordingly, the control circuit can alternately (e.g. periodically) turn the third optical field on and off so as to cause the generation of short bursts of pulsed laser light of the third optical field, e.g. as illustrated by the burst of three pulses shown in FIG. 4 C). However, it will be appreciated that the bursts may include fewer or more pulses. Also, it will be appreciated that the third optical field may be completely turned off (or on) during an extended period, e.g. responsive to an operator input.

Figure 5:
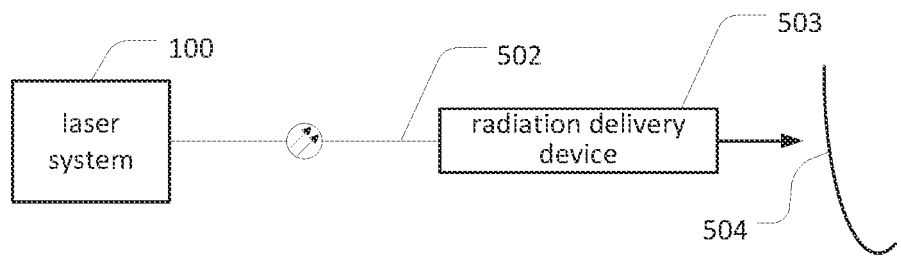
FIG. 5 schematically illustrates yet another embodiment of a medical laser system.

FIG. 5 schematically illustrates yet another embodiment of a medical laser system. The system comprises a laser source 100, e.g. as described in connection with any of FIGS. 1-3. The laser system further comprises an optical fiber 502 or other beam delivery device and a hand-held radiation delivery device 503. The optical fiber 502 has a radiation-receiving end that is coupled to an output port of the laser source and configured to receive radiation from the laser source. The optical fiber has a radiation delivery end that is coupled to the hand-held delivery device. The hand-held delivery device thus receives laser light from the laser source via the optical fiber and irradiates a user-selectable target area 504 with the received laser light.

Figure 6:
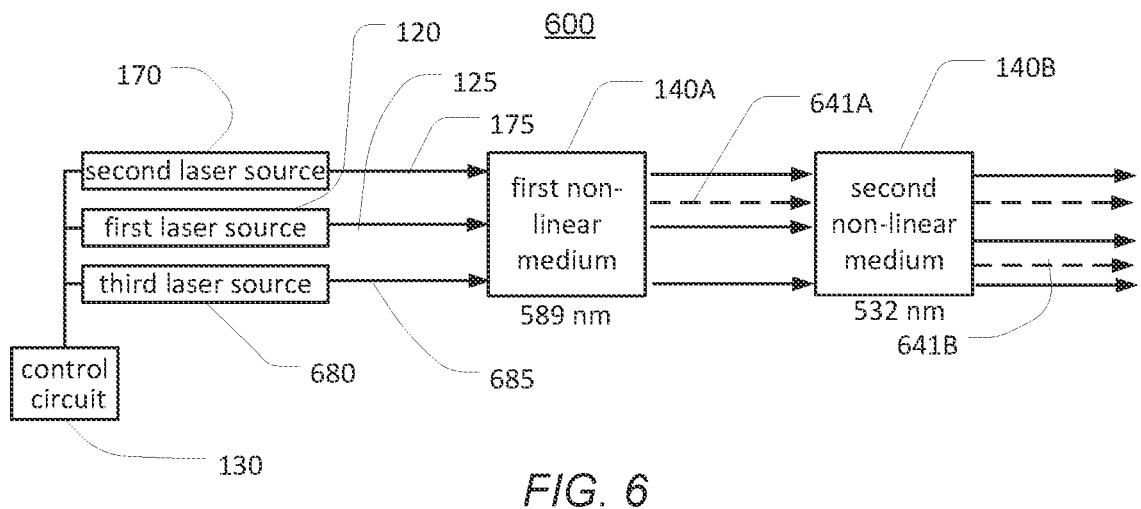
FIG. 6 schematically illustrates yet another embodiment of a medical laser system.

FIG. 6 schematically illustrates yet another embodiment of a medical laser system. The medical laser system, generally designated by reference numeral 600, comprises a first laser source 120, a second laser source 170 and a third laser source 680, e.g. each as described in connection with FIG. 1. Each laser source may be pumped by a corresponding pump source (not explicitly shown in FIG. 6) and each laser source is configured to emit respective first, second and fourth optical fields, 125, 175 and 685, respectively, each in the form of a respective pulse train. The pulse timing of the pulse trains is controlled by a control circuit 130, e.g. by controlling respective delays of trigger signals to Q-switches in laser resonator of the respective laser sources, all as described in connection with one or more of the previous embodiments.

In the present example, the first optical field 125 is horizontally polarized and has a wavelength of 1064 nm, the second optical field 175 has a wavelength of 1319 nm, and the fourth optical field 685 is vertically polarized and has a wavelength of 1064 nm.

All optical fields are directed into a first nonlinear medium 140A, e.g. by means of suitable mirrors and beam combiners. The output of the first nonlinear medium, including a third optical field 641A, if present, generated by the first nonlinear medium is directed into a second nonlinear medium 140B. The output of the second nonlinear medium, including a fifth optical field 641B, if present, generated by the second nonlinear medium is provided as an output from the system, optionally with one of more components being selected by a suitable selector. While shown as separate blocks in FIG. 6, it will be appreciated that, in some embodiments, the first nonlinear medium and the second nonlinear medium may be embodied as a single component, e.g. a single periodically poled material. Accordingly, in some embodiments, the first nonlinear medium and the second nonlinear medium may be integrated in a single nonlinear medium.

Figure 7:
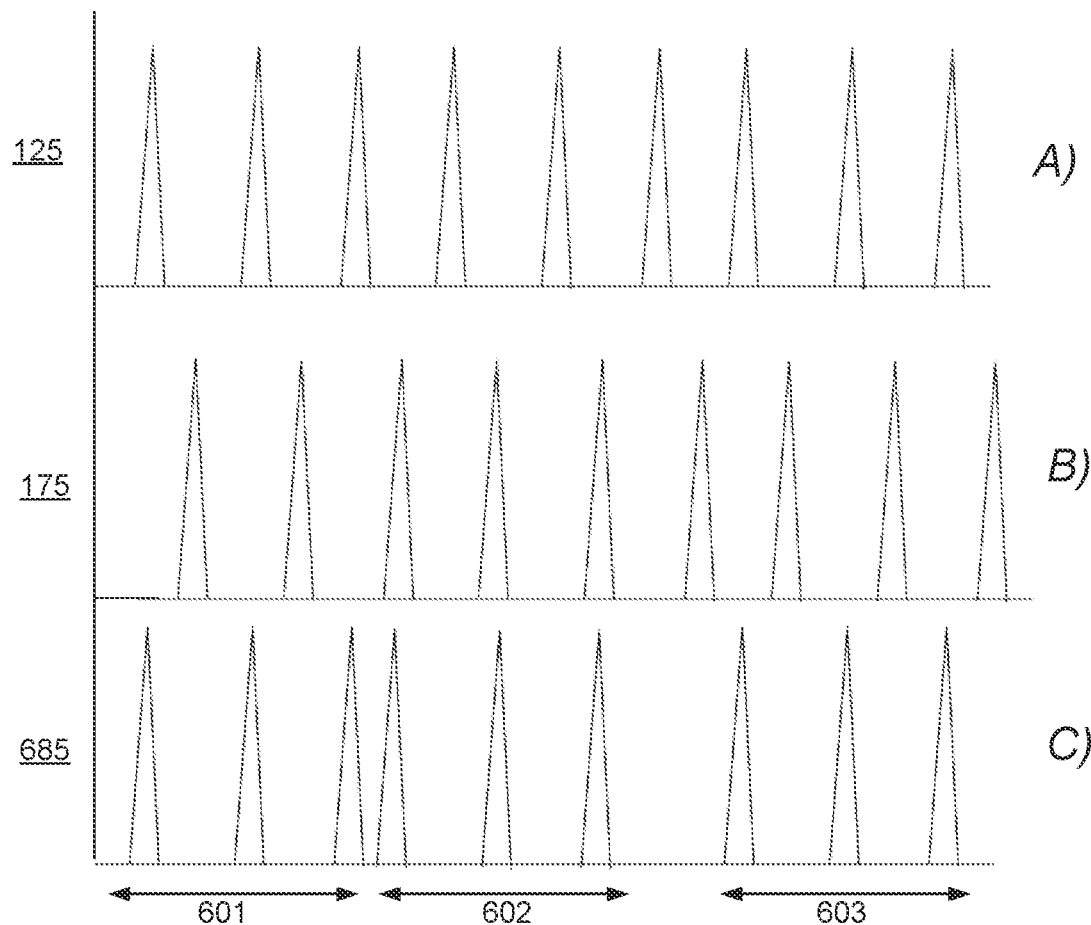
FIG. 7 illustrates operation of the embodiment of FIG. 6.

FIG. 7 illustrates operation of the embodiment of FIG. 6. In particular, FIG. 7A) shows an example of a pulse train 125 from the first laser source, FIG. 7 B) shows an example of a pulse train from 175 the second laser source and FIG. 7 C) shows an example of a corresponding pulse train 685 from the third laser source 680. As can be seen from FIGS. 7 A)-B), the pulses emitted by the first and second laser sources are substantially equidistant in time, but their relative time is such that they do not overlap in time, i.e. such that they do not interact with each other in the nonlinear media.

Similarly, FIG. 7 C) illustrates that, during periods where the pulse timing of pulse train 685 is kept constant, the pulses emitted by the third laser source are also substantially equidistant. The timing of the pulses from the third resonator is adjusted such that they selectively are either aligned with the pulses 125 (during periods 601 and 603) or with the pulses 175 (during period 602). When the pulses 685 are aligned with pulses 125, they interact in nonlinear medium 140A so as to generate light at 589 nm. When the pulses 685 are aligned with pulses 175, these interact instead in non-linear medium 175 so as to generate light at 532 nm.

Hence, by controlling the relative timing of the pulses 685, the system may be controlled to switch between outputting light at two different wavelengths.

Figure 8:
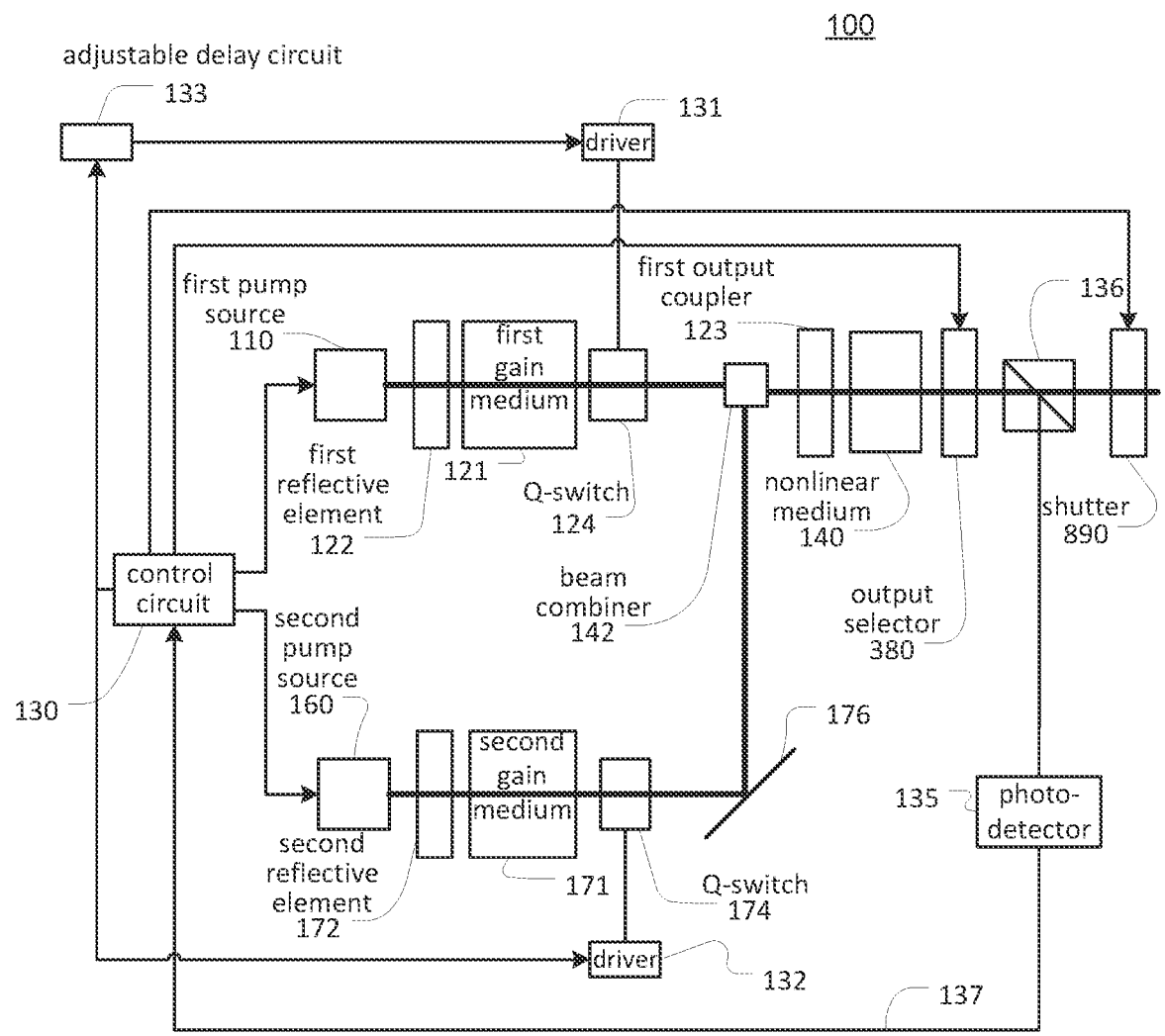
FIG. 8 schematically illustrates yet another embodiment of a medical laser system.

FIG. 8 schematically illustrates another embodiment of a medical laser system. The medical laser system of FIG. 8 is similar to the embodiment shown in FIG. 1 in that it comprises a first pump source 110, a second pump source 160, a first laser source, a second laser source, a nonlinear medium 140, drivers 131 and 132 for driving respective Q-switches 124 and 174 of the first and second laser sources, respectively, an adjustable delay circuit 133 and a control circuit 130, all as described in connection with FIG. 1, except that the first and second laser sources of the embodiment of FIG. 8 share a common output coupler 123.

In particular, the first laser source is provided in the form of a first cavity for creating a first optical field. The first cavity is defined between a first reflective element 122, such as a mirror, and partly reflective output coupler 123. The second laser source is provided in the form of a second cavity for creating a second optical field. The second cavity is defined between a second reflective element 172, such as a mirror, and the partly reflective output coupler 123. The partly reflective output coupler is partly reflective to the first and second optical fields so as to couple out parts of the circulating laser field from the respective cavities.

For example, the output coupler may be partially reflective at a first wavelength of 1064 nm and at a second wavelength of 1319 nm. In certain embodiments the reflectance for light with a wavelength of about 1064 nm and for light with a wavelength of about 1319 nm is at least about 60%, such as at least about 65% or at least about 70%, or even at least about 75% or at least about 80%. Such an output coupler may be provided as a mirror that is readily created by known arts, and is for example accomplished by coating non-absorbing, transparent substrates with multiple layers of dielectric materials such as fluorides and oxides.

The laser sources include suitable components such as a mirror 176 and a beam combiner 142 so as to direct the first and second optical fields towards the output coupler 123, e.g. along a common optical axis.

The first pump source 110, the second pump source 160, the nonlinear medium 140, the drivers 131 and 132, the Q-switches 124 and 174, the adjustable delay circuit 133 and the control circuit 130 may all be described in connection with FIG. 1 and will thus not be described in detail again.

In particular, the control circuit 130 controls the relative timing of the pulses from the first and second laser source by adjusting the adjustable delay 133. As the appropriate delay that causes the pulses from the first and second laser sources to coincide may change over time, e.g. due to drift or other instabilities of the various components of the laser system, the control circuit should preferably continuously or at least intermittently adapt the adjustable delay. To this end, the control circuit may receive a signal indicative of relative timing of the pulses in the non-linear medium and adapt the adjustable delay based on the received signal.

Figure 9:
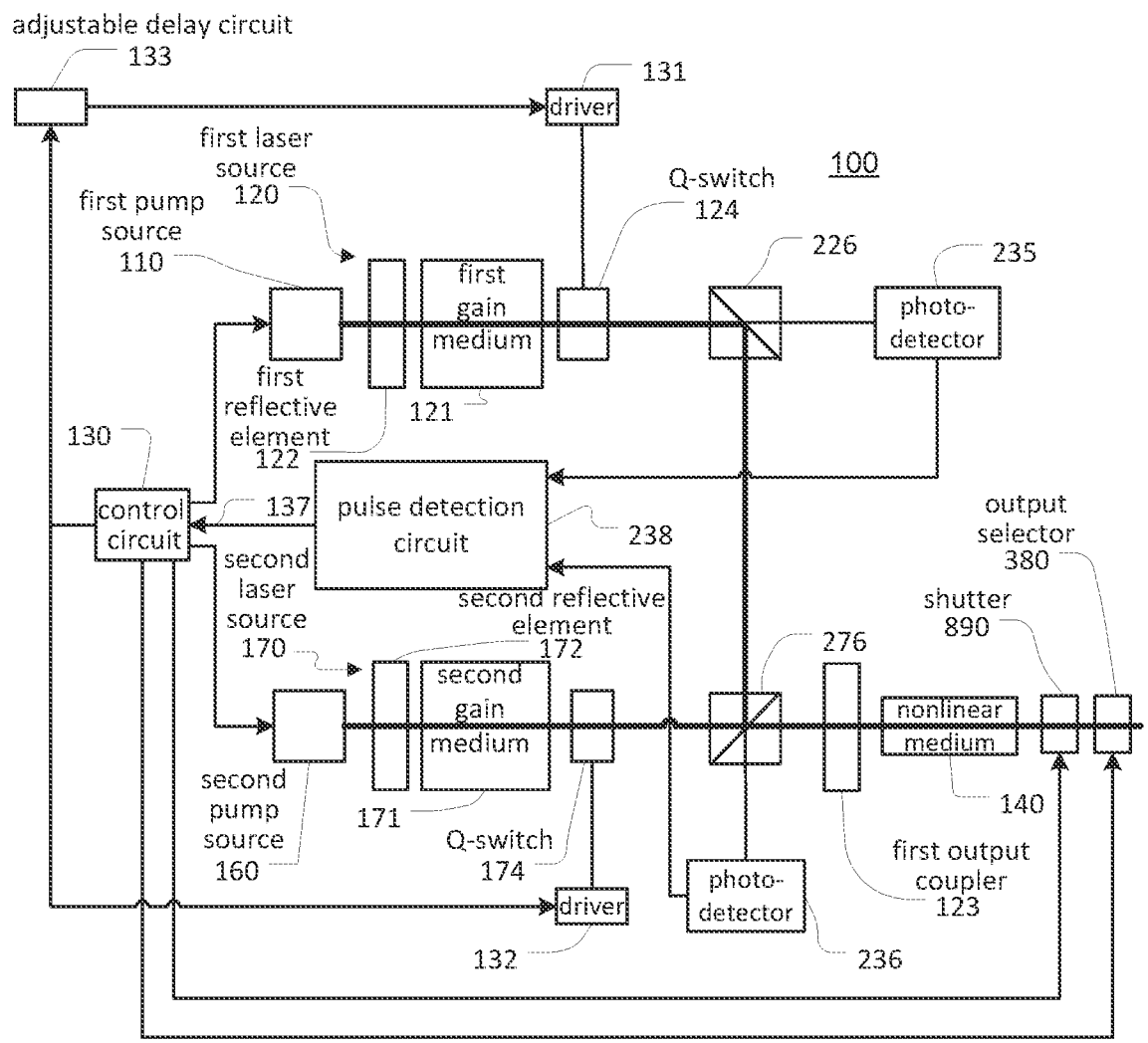
FIG. 9 schematically illustrates yet another embodiment of a medical laser system.

To this end, the embodiment of FIG. 8 includes a beam splitter 136 which receives the output 135 from the nonlinear medium 140 and which directs a minor portion of the output 141 towards a photodetector 135, e.g. as described in connection with FIG. 1. The output from the photodetector is fed to the control circuit 130 as a signal 137 that is indicative of the intensity of the third optical field, i.e. indicative of the efficiency of the nonlinear process in the nonlinear medium. The control circuit may thus adjust the delay 133 so as to maximize the detected intensity of the third optical field. It will be appreciated that the laser system may be configured such that the photodetector 135 receives and detects the first and/or second wavelength and the control circuit may then be configured to adjust the delay 133 so as to minimize the content of the first and/or second wavelength in the output 141 from the nonlinear medium 140. Alternatively, control of the Q-switches may be based on measurements of the first and second optical fields in the laser sources, e.g. as shown in FIG. 9, or at the output of the laser sources.

The laser system of FIG. 8 further includes an output selector 380 positioned in the beam path of the output 141 from the nonlinear medium 140, e.g. as described in connection with FIG. 3. The output selector 380 is operatively coupled to the control circuit 130 such that the control circuit controls operation of the output selector 380.

The laser system of FIG. 8 further comprises a shutter 890 or other exposure control device which is controlled by the control circuit 130 and configured to selectively either block the output beam or allow the output beam to pass. Alternatively or additionally, as described in respect of e.g. FIG. 1, the relative timing of the pulse trains of the first and second optical fields may be used as an exposure control mechanism. Nevertheless, in some embodiments, in particular when very fast on/off switching is not required, a mechanical shutter 890 may be a cost effective alternative.

In the embodiment of FIG. 8, the shutter 890 is positioned downstream of the output selector 380. However, alternatively, the shutter 890 may be positioned upstream of the output selector 380, e.g. as shown in FIG. 9. In alternative embodiments, other positions of the shutter 890 are possible, e.g. upstream of the nonlinear medium 140. For example, the system may comprise two shutters positioned in the respective beam paths that feed into the beam combiner 142, e.g. such that the first and second optical fields can each selectively and individually be blocked.

FIG. 9 schematically illustrates another embodiment of a medical laser system. The medical laser system of FIG. 9 is similar to the embodiment shown in FIG. 8, except that the output selector 380 is positioned downstream relative to the shutter 890, and except that the control of the Q-switches 124 and 174 is based on measurements of the individual optical fields in the cavities.

To this end, the laser system comprises beam splitters 226 and 276 and photodetectors 235 and 236. Beam splitter 226 directs a minor portion of the first optical field towards photodetector 235 while beam splitter 276 directs a minor portion of the second optical field towards photodetector 236. The photodetectors 235 and 236 forward their respective detection signals to a pulse detection circuit 238. The pulse detection circuit detects the laser pulses of the pulse trains of the first and second optical fields, respectively, and determines the time lag between the respective pulses. The pulse detection circuit then forwards a signal 137 to the control circuit 130 indicative of the detected time lag. The control circuit may thus select the adjustable delay 133 such that the time lag is minimized in order to cause creation of the third optical field.

Embodiments of the laser control described herein can be implemented by means of hardware comprising several distinct elements, and/or at least in part by means of a suitably programmed microprocessor. In the apparatus claims enumerating several means, several of these means can be embodied by one and the same element, component or item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, elements, steps or components but does not preclude the presence or addition of one or more other features, elements, steps, components or groups thereof.

The invention claimed is:

1. A medical laser system, comprising:
   a first laser source comprising first laser resonator, at least a first gain medium for generating a first optical field, and at least one first Q-switch configured to control a resonance quality of the first laser resonator;
   a control circuit configured to control the first Q-switch to cause the first laser resonator to generate the first optical field as a first pulse train of laser pulses;
   a second laser source for generating a second optical field as a second pulse train of laser pulses;
   at least one nonlinear medium for generating a third optical field by a nonlinear interaction between the first optical field and the second optical field;
   a sensor configured to detect a property of at least one of the optical fields;
   wherein the control circuit is configured to control operation of the first Q-switch so as to adjust a relative timing of the laser pulses of the first pulse train and the laser pulses of the second pulse train responsive to the detected property; and
   wherein the control circuit comprises an adjustable delay circuit and the control circuit is configured to generate a trigger signal and to forward the trigger signal to the adjustable delay circuit.

2. The medical laser system according to claim 1, wherein the adjustable delay circuit is configured to forward a delayed version of the trigger signal, delayed by an adjustable delay relative to the trigger signal, to the first Q-switch; and wherein the control circuit is configured to adjust the adjustable delay responsive to the detected property.

3. The medical laser system according to claim 1, wherein the detected property represents an output power of the third optical field or a relative timing of the laser pulses of the first pulse train and the laser pulses of the second pulse train.

4. The A medical laser system according to claim 1, wherein the control circuit is configured to control:
   the relative timing such that the laser pulses of the first pulse train temporally overlap in the nonlinear medium with respective laser pulses of the second pulse train; or
   the relative timing so as to cause generation of the third optical field, or
   the relative timing so as to selectively cause generation of the third optical field, or
   a relative timing of laser pulses of the respective pulse trains inside the at least one nonlinear medium so as to selectively cause generation of one or more of the third and of further optical fields.

5. The medical laser system according to claim 1 wherein the control circuit is configured responsive to a first signal, to selectively control the relative timing such that the laser pulses of the first pulse train temporally overlap in the nonlinear medium with respective laser pulses of the second pulse train so as to cause generation of the third optical field; and wherein the control circuit is configured, responsive to a second signal, to selectively control the relative timing such that the laser pulses of the first pulse train do not temporally overlap in the nonlinear medium with respective laser pulses of the second pulse train so as to prevent generation of the third optical field.

6. The medical laser system according to claim 5, wherein the control circuit is configured to determine a second relative timing that causes the laser pulses of the first pulse train to temporally overlap in the nonlinear medium with respective laser pulses of the second pulse train so as to cause generation of the third optical field; and wherein during a period where the control circuit is configured to control the relative timing to be a first relative timing that causes the laser pulses of the first pulse train to not temporally overlap in the nonlinear medium with respective laser pulses of the second pulse train so as to prevent generation of the third optical field, the control circuit is configured, responsive to the first signal, to switch the relative timing from the first relative timing to the determined second relative timing.

7. The medical laser system according to claim 1, wherein the first optical field has a first wavelength, the second optical field has a second wavelength and the third optical field has a third wavelength different from the first and second wavelengths.

8. The medical laser system according to claim 7, wherein the control circuit is configured to control the relative timing so as to include the third wavelength into an output radiation of the laser system or wherein the control circuit is configured, responsive to a wavelength selection command, to selectively control the relative timing so as to selectively include the third wavelength into an output radiation of the laser system.

9. The medical laser system according to claim 7, further comprising an output selector for selectively blocking radiation of at least one of the first wavelength, the second wavelength, and the third wavelength from being included in the output radiation of the laser system, and wherein the control circuit is configured to selectively activate the output selector in response to a wavelength selection command.

10. The medical laser system according to claim 1, wherein the medical laser system is a dermatological laser system.

11. The medical laser system according to claim 1, further comprising a hand-held radiation delivery device defining at least one optical output port for delivering the third optical field to an output.

12. The laser system according to claim 11, wherein the medical laser system is configured to selectively deliver the first, the second and/or the third optical fields by the optical output port.

13. The medical laser system according to claim 11, wherein the medical laser system is configured to selectively deliver the first, the second and/or the third optical fields to a plurality of target locations.

14. The medical laser system according to claim 13, wherein the medical laser system is configured to selectively deliver an optical field of different wavelengths to different target locations.

15. The medical laser system according to claim 1, wherein the medical laser system is operable to feed more than two optical fields into at least one nonlinear medium, and wherein each optical field defines a respective pulse train of laser pulses.

16. The medical laser system according to claim 1, further comprising an exposure control device configured to selectively allow radiation from the laser system to pass toward a target area.

17. The medical laser system according to claim 16, further comprising an output selector for selectively blocking radiation of at least one of a first wavelength, second wavelength, and third wavelength in the output radiation of the laser system, wherein the control circuit is configured to selectively activate the output selector in response to a wavelength selection command, and wherein the exposure control device is positioned upstream from the output selector along the radiation path.

18. The medical laser system according to claim 16, further comprising an output selector for selectively blocking radiation of at least one of a first wavelength, second wavelength, and third wavelength to be from being included in the output radiation of the laser system, wherein the control circuit is configured to selectively activate the output selector in response to a wavelength selection command, and wherein the exposure control device is positioned downstream from the output selector along the radiation path.

19. A medical laser system, comprising:
a first laser source comprising first laser resonator, at least a first gain medium for generating a first optical field, and at least one first Q-switch configured to control a resonance quality of the first laser resonator, the first optical field having a first wavelength;
a control circuit configured to control the first Q-switch to cause the first laser resonator to generate the first optical field as a first pulse train of laser pulses;
a second laser source for generating a second optical field as a second pulse train of laser pulses, the second optical field having a second wavelength;
at least one nonlinear medium for generating a third optical field by a nonlinear interaction between the first optical field and the second optical field, the third optical field having a third wavelength different from the first and second wavelengths;
a sensor configured to detect a property of at least one of the optical fields;
wherein the control circuit is configured to control operation of the first Q-switch so as to adjust a relative timing of the laser pulses of the first pulse train and the laser pulses of the second pulse train responsive to the detected property, and
wherein the control circuit is configured to selectively control the relative timing of the laser pulses of the first pulse train and the laser pulses of the second pulse train such that the laser pulses of the first pulse train and the second pulse train do not temporally overlap in the nonlinear medium so as to prevent generation of the third optical field.

20. The medical laser system according to claim 19, wherein the control circuit is configured, responsive to a first signal, to selectively control the relative timing such that the laser pulses of the first pulse train temporally overlap in the nonlinear medium with respective laser pulses of the second pulse train so as to cause generation of the third optical field; and wherein the control circuit is configured, responsive to a second signal, to selectively control the relative timing such that the laser pulses of the first pulse train do not temporally overlap in the nonlinear medium with respective laser pulses of the second pulse train to prevent generation of the third optical field.

21. The medical laser system according to claim 20, wherein the control circuit is configured to determine a second relative timing that causes the laser pulses of the first pulse train to temporally overlap in the nonlinear medium with respective laser pulses of the second pulse train so as to cause generation of the third optical field; and wherein during a period where the control circuit is configured to control the relative timing to be a first relative timing that causes the laser pulses of the first pulse train to not temporally overlap in the nonlinear medium with respective laser pulses of the second pulse train so as to prevent generation of the third optical field, the control circuit is configured, responsive to the first signal, to switch the relative timing from the first relative timing to the determined second relative timing.

22. A medical laser system, comprising:
a first laser source comprising first laser resonator, at least a first gain medium for generating a first optical field; and at least one first Q-switch configured to control a resonance quality of the first laser resonator, the first optical field having a first wavelength;
a control circuit configured to control the first Q-switch to cause the first laser resonator to generate the first optical field as a first pulse train of laser pulses;
a second laser source for generating a second optical field as a second pulse train of laser pulses, the second optical field having a second wavelength;
at least one nonlinear medium for generating a third optical field by a nonlinear interaction between the first optical field and the second optical field, the third optical field having a third wavelength different from the first and second wavelengths;
a sensor configured to detect a property of at least one of the optical fields;
an exposure control device configured to selectively allow radiation from the laser system to pass toward a target area; and
an output selector for selectively blocking radiation of at least one of the first wavelength, the second wavelength, and the third wavelength from being included in the output radiation of the laser system;
wherein the control circuit is configured to control operation of the first Q-switch so as to adjust a relative timing of the laser pulses of the first pulse train and the laser pulses of the second pulse train responsive to the detected property; and
wherein the control circuit is configured to selectively activate the output selector in response to a wavelength selection command; and wherein the exposure control device is positioned upstream from the output selector along the radiation path.

23. A medical laser system, comprising:
a first laser source comprising first laser resonator, at least a first gain medium for generating a first optical field; and at least one first Q-switch configured to control a resonance quality of the first laser resonator;
a control circuit configured to control the first Q-switch to cause the first laser resonator to generate the first optical field as a first pulse train of laser pulses, the first optical field having a first wavelength different;
a second laser source for generating a second optical field as a second pulse train of laser pulses, the second optical field having a second wavelength;
at least one nonlinear medium for generating a third optical field by a nonlinear interaction between the first optical field and the second optical field, the third optical field having a third wavelength different from the first and second wavelengths;
a sensor configured to detect a property of at least one of the optical fields;
an exposure control device configured to selectively allow radiation from the laser system to pass toward a target area; and
an output selector for selectively blocking radiation of at least one of first wavelength, the second wavelength, and the third wavelength from being included in the output radiation of the laser system; and
wherein the control circuit is configured to control operation of the first Q-switch so as to adjust a relative timing of the laser pulses of the first pulse train and the laser pulses of the second pulse train responsive to the detected property; and
wherein the control circuit is configured to selectively activate the output selector in response to a wavelength selection command; and wherein the exposure control device is positioned downstream from the output selector along the radiation path.

24. A medical laser system, comprising:
a first laser source comprising first laser resonator, at least a first gain medium for generating a first optical field; and at least one first Q-switch configured to control a resonance quality of the first laser resonator;
a control circuit configured to control the first Q-switch to cause the first laser resonator to generate the first optical field as a first pulse train of laser pulses;
a second laser source for generating a second optical field as a second pulse train of laser pulses;
at least one nonlinear medium for generating a third optical field by a nonlinear interaction between the first optical field and the second optical field;
a sensor configured to detect a property of at least one of the optical fields;
wherein the control circuit is configured to control operation of the first Q-switch so as to adjust a relative timing of the laser pulses of the first pulse train and the laser pulses of the second pulse train responsive to the detected property; and
wherein the first optical field has a first wavelength, the second optical field has a second wavelength, and the third optical field has a third wavelength different from the first and second wavelengths; and
an output selector for selectively blocking radiation of at least one of the first wavelength, second wavelength, and third wavelength from being included in the output radiation of the laser system, and wherein the control circuit is configured to selectively activate the output selector in response to a wavelength selection command.

25. A medical laser system, comprising:
a first laser source comprising first laser resonator, at least a first gain medium for generating a first optical field; and at least one first Q-switch configured to control a resonance quality of the first laser resonator;
a control circuit configured to control the first Q-switch to cause the first laser resonator to generate the first optical field as a first pulse train of laser pulses;
a second laser source for generating a second optical field as a second pulse train of laser pulses;
at least one nonlinear medium for generating a third optical field by a nonlinear interaction between the first optical field and the second optical field;
a sensor configured to detect a property of at least one of the optical fields;
wherein the control circuit is configured to control operation of the first Q-switch so as to adjust a relative timing of the laser pulses of the first pulse train and the laser pulses of the second pulse train responsive to the detected property; and
wherein the medical laser system is operable to feed more than two optical fields into the at least one nonlinear medium, each optical field defining a respective pulse train of laser pulses.

* * * * *

UNITED STATES PATENT AND TRADEMARK OFFICE
CERTIFICATE OF CORRECTION

| | | |
|---|---|---|
| PATENT NO. | : 12,053,640 B2 | |
| APPLICATION NO. | : 17/253039 | |
| DATED | : August 6, 2024 | |
| INVENTOR(S) | : Morten Thorhauge et al. | |

It is certified that error appears in the above-identified patent and that said Letters Patent is hereby corrected as shown below:

In the Claims

At Column 29, Line 34 (Claim 18), please delete "and third wavelength to be from being included" and insert --and third wavelength from being included-- therefor.

Signed and Sealed this
Seventeenth Day of September, 2024

Katherine Kelly Vidal
*Director of the United States Patent and Trademark Office*